United States Patent [19]
Dinh et al.

[11] Patent Number: 6,074,381
[45] Date of Patent: Jun. 13, 2000

[54] CYLINDRICAL ROLLER STENT CRIMPER APPARATUS WITH RADIATION SHIELD

[75] Inventors: Minh Q. Dinh, Union City; Todd H. Turnlund, Sunnyvale; Thomas H. Campbell, Redwood City, all of Calif.

[73] Assignee: IsoStent, Inc., Belmont, Calif.

[21] Appl. No.: 09/177,668

[22] Filed: Oct. 22, 1998

[51] Int. Cl.[7] .............................. A61B 17/00; A61F 11/00
[52] U.S. Cl. .................... 606/1; 606/198; 29/235
[58] Field of Search ................... 606/1, 108, 198, 606/191, 194; 53/204, 209, 211, 213, 214; 29/235

[56] References Cited

U.S. PATENT DOCUMENTS 5,437,083  8/1995  Williams et al. .
5,836,952  11/1998  Davis et al. .

Primary Examiner—Michael Buiz
Assistant Examiner—William Lewis
Attorney, Agent, or Firm—Beyer Weaver & Thomas

[57] ABSTRACT

A stent loading apparatus for loading a deformable stent onto a deployment device. The stent loading apparatus includes an elastic member defining a passage therein formed for longitudinal receipt of the deformable stent in an uncrimped condition. A first member includes a first compression region; and a second member includes a second compression region positioned substantially adjacent the first compression region at a first position. At this first position, the elastic member and the deformable stent in the uncrimped condition may be received between the opposed first and second compression regions. The first compression region and the second compression region are further configured to provide rolling support and compression of the elastic member during relative movement between the first position and a second position for rolling radial compression of the deformable stent onto the deployment device.

55 Claims, 12 Drawing Sheets

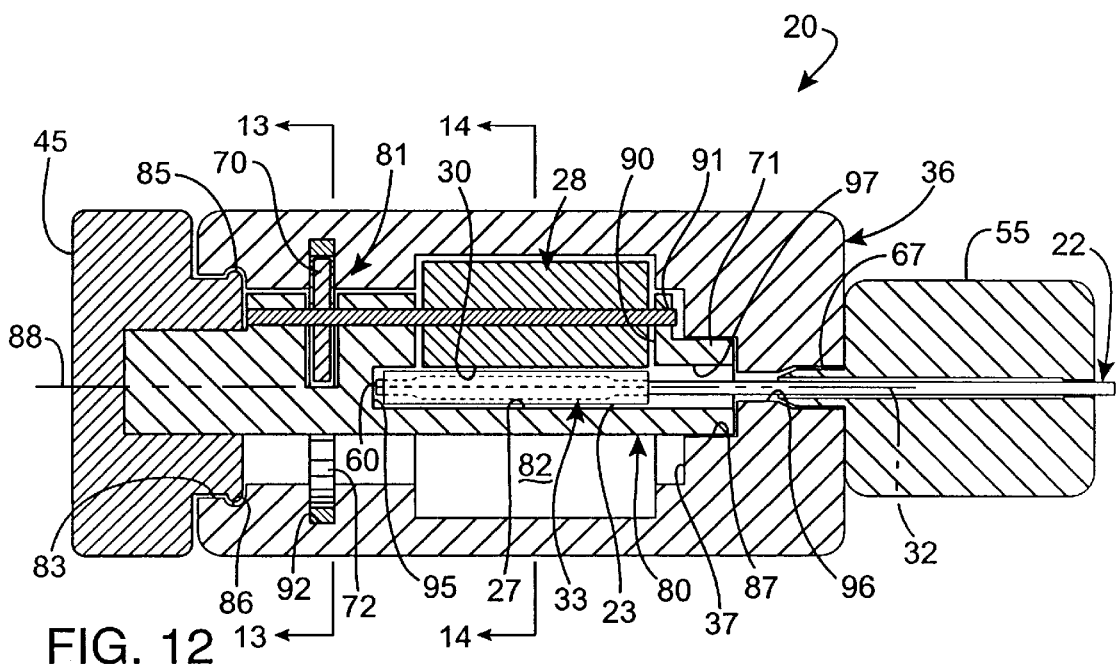
FIG. 12
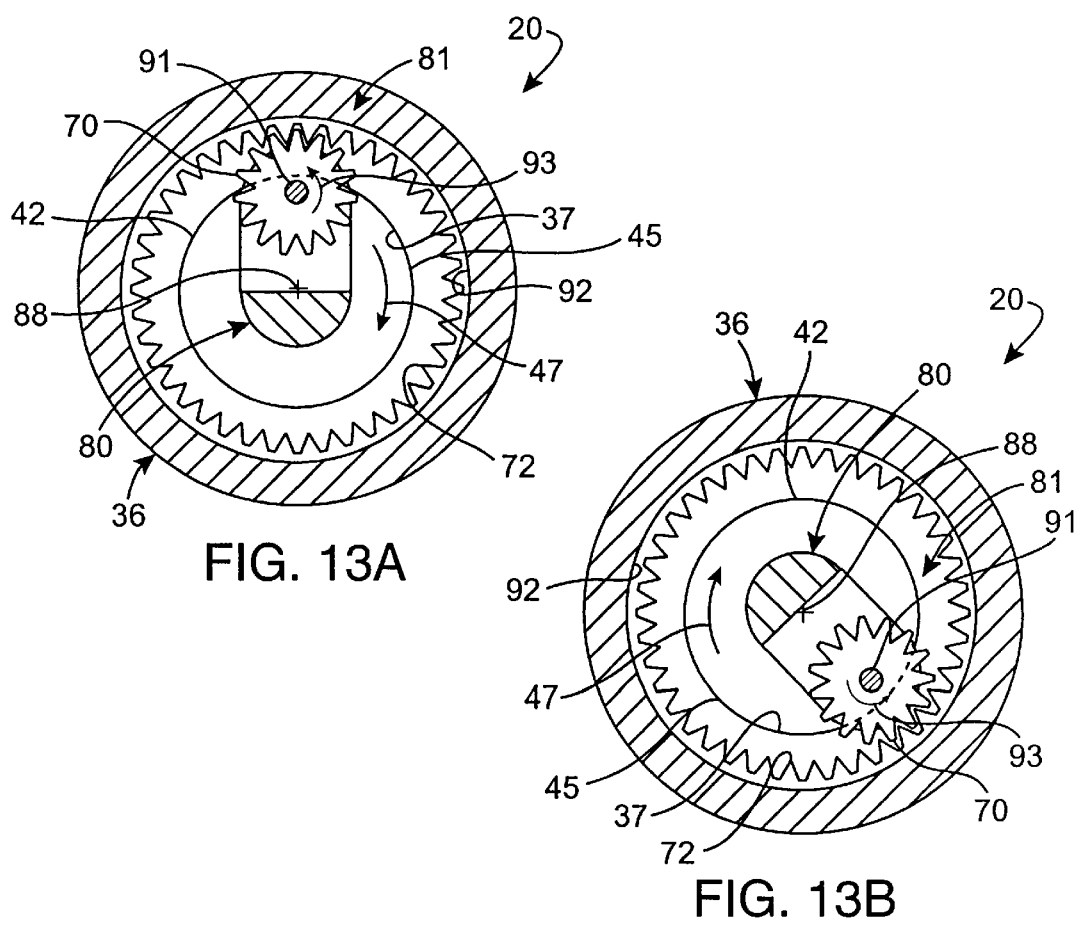
FIG. 13A
FIG. 13B

CYLINDRICAL ROLLER STENT CRIMPER APPARATUS WITH RADIATION SHIELD

TECHNICAL FIELD

The present invention relates, generally, to intravascular stents and, more particularly, to stent crimping apparatus with radiation shields for radioactive stents.

BACKGROUND ART

Percutaneous Transluminal Angioplasty (PTA) is a medical procedure for widening a stenosis or constriction of a bodily passage. The most common application is to widen the passage of a blood vessel, such as an artery, which has been constricted by the build-up of cholesterol fats or atherosclerotic plaque. When this medical procedure is applied to a coronary artery, it is referred to as Percutaneous Transluminal Coronary Angioplasty (PTCA).

Typically, a tip mounted balloon of a balloon catheter is advanced over a guidewire to the stenosis. Once the balloon catheter is properly position, the balloon is inflated to compress the plaque against the vessel walls and widen the stenosis. Problems occur, however, when the dilatation of the occlusion forms fissures, flaps and/or dissections which may ultimately cause reclosure or restenosis of the vessel.

To maintain vessel patency and/or strengthen the area undergoing angioplasty or other treatment, an intravascular prosthesis may be employed. These devices are usually introduced percutaneously, transported transluminally and positioned at a desired location within the widened stenosis of the patient. One form of an intravascular prosthesis is a radially expandable stent device which is typically positioned at the tip of a balloon catheter and is implanted by expansion of the balloon when the balloon and stent device are at the desired location. Expansion of the balloon portion of the catheter can simultaneously compress plaque at that location and expand the stent to its proper implantation size. The balloon portion of the catheter is then deflated and withdrawn from the vessel, leaving the implanted stent as a permanent scaffold to reduce the chance of restenosis.

To adequately mount an unexpanded stent onto the balloon catheter for delivery into the patient, the stent is "crimped" or otherwise radially collapsed sufficiently to attach it to the balloon. One technique is to crimp the stent onto the balloon catheter through the use of a pair of modified plier-like tools which crimp down on the unexpanded stent. The performance of these tools, however, is not completely satisfactory since there is still a wide divergence between application force, profile and stent diameter. Problems arise when excessive crimping forces are applied to the crimp pliers which can damage the stent and/or balloon catheter. This is especially problemsome given the minute size of the stents which are typically on the order of about one (1) mm to four (4) mm in diameter before crimping. Moreover, non-uniformity of the crimping may be experienced as well as the inability to determine when a reliable and uniform crimp has been achieved.

In other instances, the stents may be pre-crimped or preattached onto their associated delivery balloon at the time of production by the manufacturer. While these devices more uniformly control crimping quality, a large inventory of stent-bearing angioplasty catheters must be maintained to accommodate the variety of stent types, diameters and stent lengths for each balloon catheter type. Thus, maintaining such an inventory is not only difficult to store, but can be very expensive as well.

One of the most favored crimping techniques is manual crimping performed by the physician in the catheter laboratory. This process enables the physician to "feel" the crimp to determine the crimp quality. The proper crimping of a stent about a balloon catheter, however, is a technique acquired only through practice and can be affected by a variety of subjective conditions. Too much or too little pressure may be applied and the balloon and/or stent may be damaged, lost, or may not otherwise perform as desired during the procedure. In contrast, the physician may not apply sufficient crimping pressure to the stent to load it onto the balloon. During advancement through the vessel or upon deployment, an insufficiently crimped stent may slip or rotate on the catheter during, or in the worst case scenario, come off the balloon catheter entirely; the result of which is not desirable. Moreover, when applying radioactive or radioisotope embedded stents, direct manual handling by physicians and laboratory technicians should be avoided.

DISCLOSURE OF INVENTION

Accordingly, a stent loading apparatus is provided for loading a deformable stent onto a deployment device. The stent loading apparatus includes an elastic member defining a passage therein formed for longitudinal receipt of the deformable stent in an uncrimped condition. The stent loading apparatus further includes a first member having a first compression region; and a second member having a second compression region positioned substantially adjacent the first compression region at a first position. At this position, the elastic member and the deformable stent in the uncrimped condition may be received between the opposed first and second compression regions. The first compression region and the second compression region are further configured to provide rolling support and compression of the elastic member during relative movement between the first position and a second position to radially compress the deformable stent onto the deployment device.

In another aspect of the present invention, a stent loading apparatus is provided for loading a deformable stent onto a deployment device including a crimper body including a curvilinear first compression wall defining a bore portion; and a spindle member having a curvilinear second compression wall extending into the bore portion adjacent the first compression wall. The spindle member is rotatably coupled to the crimper body for relative rotation of the first compression wall and the second compression wall between a first position and a second position. In the first position, the first compression wall and the second compression wall are sufficiently spaced to enable receipt of the deformable stent therebetween. In the second position, the opposed first and second compression walls are sufficiently spaced to roll and radially compress the stent onto the deployment device.

In one configuration, a gear assembly is included which is formed to cooperate with the crimper body, the spindle member and the deployment device to provided for rolling support of the stent between the first position and the second position. The gear assembly preferably includes a drive gear coupled to the crimp roller, an internal gear coupled to the crimper body, and a spur gear driveably meshed between the drive gear and the internal gear. The spur gear is further coupled to the deployment device to facilitate movement of the stent between the first position and the second position.

In yet another aspect of the present invention, a stent loading apparatus includes a roller housing having a first compression wall defining a longitudinally extending groove portion, and a crimp roller rotatably coupled to the roller housing. The crimp roller further includes a substantially cylindrical second compression wall positioned adjacent and substantially parallel to the groove portion. A drive mechanism is coupled between the crimp roller and the roller housing for relative rotation of the second compression wall and the first compression wall between a first position and a second position. Similar to the previous configuration, in the first position, the first compression wall and the second compression wall are sufficiently spaced to enable receipt of the deformable stent therebetween. In the second position, the opposed first and second compression walls are sufficiently spaced to roll and radially compress the stent onto the deployment device.

Another aspect of the present invention, a stent apparatus is provided for use with loading onto a deployment device. The stent apparatus includes an uncrimped elongated stent having an uncrimped diameter; and a shrink tube having a longitudinal length longer than the stent. The shrink tube, in an unshrunk condition, is formed to have an unshrunk diameter larger than the uncrimped diameter of the stent for sliding receipt of the stent therein. After the shrinking procedure, the shrink tube is of a shrunk diameter smaller than the uncrimped diameter to secure the shrink tube longitudinally around the stent for support thereof for alignment and positioning of the deployment device in the uncrimped stent.

One other aspect of the present invention provides a shielded stent crimping assembly for loading a radioactive stent onto a deployment device. This assembly includes a crimping mechanism adapted to crimp the radioactive stent onto the deployment device. A shielded crimper body defines a bore portion formed for receipt of the radioactive stent and the crimping mechanism therein. The crimper body and the crimping mechanism cooperate to substantially prevent the passage of radiation from the bore portion during crimping of the stent by the crimping mechanism.

A method of crimping a stent in onto a deployment device is further provided comprising the steps of: inserting the uncrimped stent into an elastic tube having a diameter larger than the diameter of the uncrimped stent; and compressing the elastic tube until the opposed interior walls of the elastic tube contact the exterior walls of the uncrimped stent. The present inventive method further includes the step of compressibly rolling the elastic tube and the uncrimped stent from an uncrimped condition to a crimped condition until the compressed stent is mounted to the deployment device.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 12 is a side elevation view, in cross-section, of a fifth embodiment of a stent loading apparatus of the present invention.

FIGS. 13A and 13B are a sequence of enlarged front elevation views, in cross-section, of the fifth embodiment of the stent loading apparatus taken substantially along the plane of the line 13—13 in FIG. 12, and illustrating a gear assembly during crimping movement between the first position and the second positions.

BEST MODE OF CARRYING OUT THE INVENTION

Figure 3:
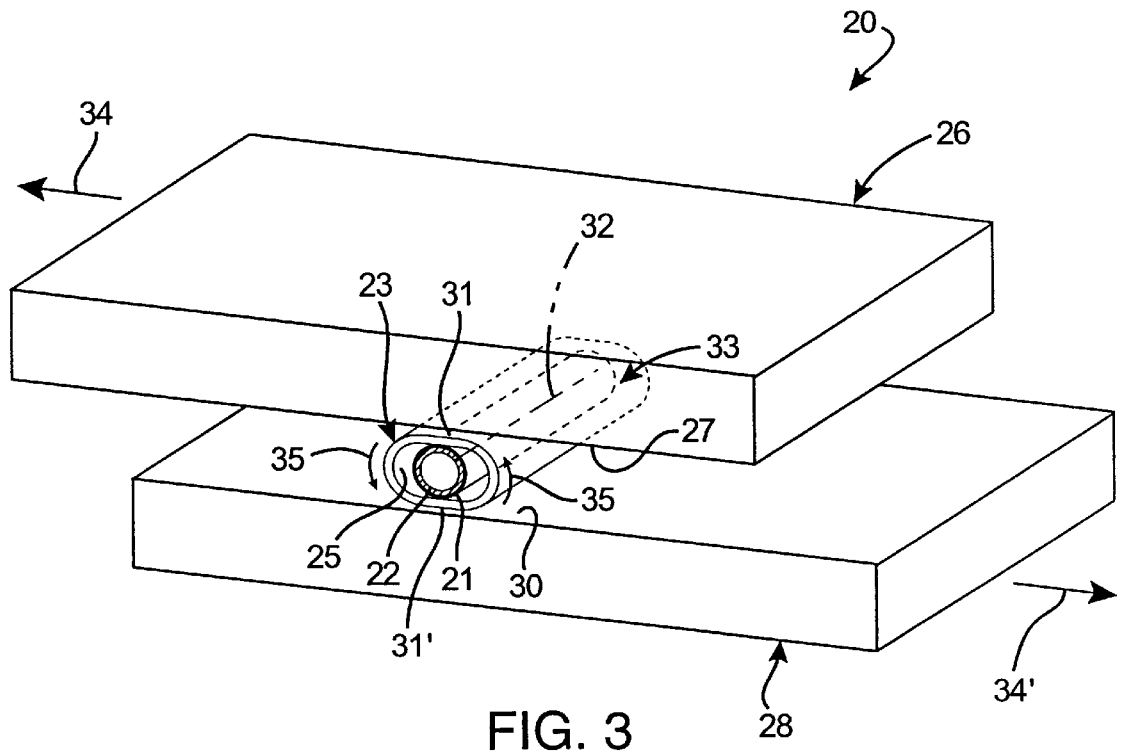
FIG. 3 is a fragmentary top perspective view of the first embodiment of the stent loading apparatus of FIG. 1 illustrating the stent being radially compressed and rolled onto the balloon catheter between a first member and a second member.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figures 1, 2:
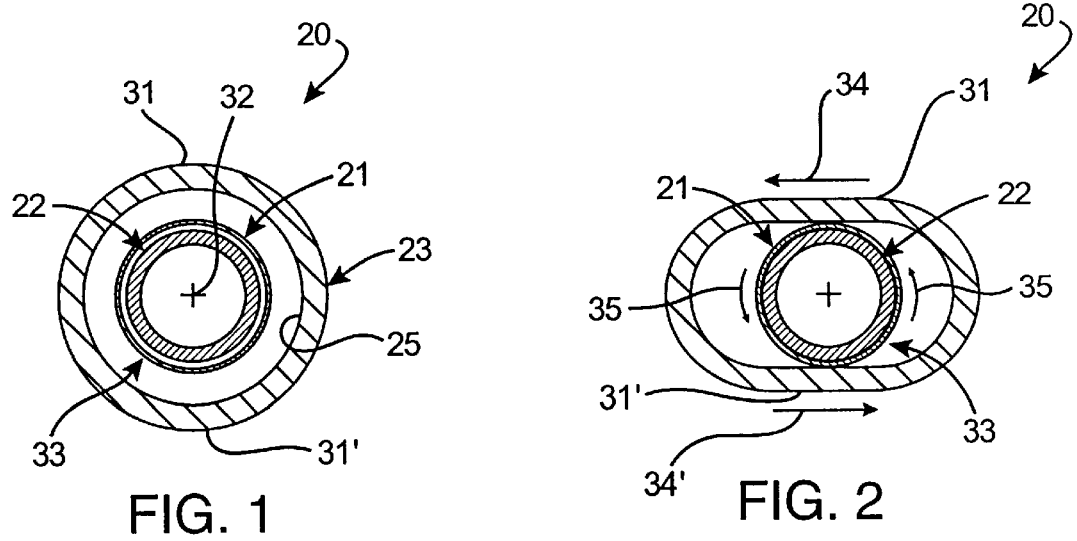
FIG. 1 is an enlarged front elevation view, in cross-section, of a first embodiment of a stent loading apparatus constructed in accordance with the present invention oriented in a first position to enable receipt of an uncrimped stent and balloon catheter therein.
FIG. 2 is a front elevation view, in cross-section, of the first embodiment of the stent loading apparatus of FIG. 1 oriented in a second position to radially compress and roll the stent onto the balloon catheter.

Attention is now directed to FIGS. 1–3, where a stent loading apparatus, generally designated 20, is provided for crimping and mounting a deformable stent 21 onto a deployment device 22 (only a portion of which is illustrated). The stent loading apparatus 20 includes an elastomeric or elastic member 23 defining a passage 25 therein formed for longitudinal receipt of the deformable stent 21 in an uncrimped condition (FIG. 1). The stent loading apparatus 20 further includes a first member 26 having a first compression region 27, and a second member 28 having a second compression region 30 positioned substantially adjacent the first compression region 27 at a first position (FIG. 1). In this arrangement, the elastic member 23 and the deformable stent 21 in the uncrimped condition may be received between the first compression region 27 and opposite second compression region 30. These opposed compression regions 27 and 30 are further configured to provide rolling support and compression of the elastic member 23 during relative movement between the first position and a second position (FIGS. 2 and 3) to radially compress the deformable stent 21 onto the deployment device 22.

Accordingly, a stent loading apparatus is provided for crimping an uncrimped stent onto a deployment device, such as a balloon catheter, which employs an elastic member to facilitate radial compression and rolling support of the stent until it is properly mounted to the balloon in a crimped condition. This elastic tube, in combination with the compressive rolling action, exerts a uniform distribution of opposed and compressive radial forces along the stent. Such uniformity of the crimp in the longitudinal direction assures maintenance of the stent on the deployment device, as well as facilitate proper expansion of the stent during deployment.

In the preferred form, the elastic member 23 is provided by an elastic tube which is sufficiently radially flexible so that it may be compressed against the outer walls of the uncrimped stent 21. Moreover, the elastic tube must be capable of compressively gripping the stent when sufficient rolling pressure is applied to the exterior walls 31, 31' of the elastic tube 23 to cause a rolling motion of the stent about its longitudinal axis 32. Such materials (rubbers, thermoplastics, and thermosets) include silicon, natural rubber, polyurethane, polyethylene, nylon, poly propylene, polyester, or the like.

The passage interior diameter of the elastic tube 23 is preferably sufficiently large to enable uninterfered insertion of the uncrimped stent 21 therein when the elastic tube is in a relaxed, uncompressed condition. Thus, the diameter of the tube passage 25 is preferably in the range of about 1% to about 200% larger than the outer diameter of the uncrimped stent. More preferably, the passage diameter is about 60% larger than the uncrimped stent diameter.

As viewed in FIGS. 1 and 2, the radial thickness of the elastic tube 23 is significantly greater than the radial thickness of the stent by about a 10:1 ratio. This dimensional difference, together with the nature of the elastic material, facilitates protection of the stent during the compressive rolling action. The elastic tube 23 is also preferably longer than the uncrimped stent and balloon combination (hereinafter, the "stent assembly 33") so that the compressive rolling movement can be more uniformly distributed longitudinally therealong. However, it will be understood that the tube length may be shorter than the stent assembly 33 without departing from the true spirit and nature of the present invention.

The compressive rolling forces urged upon the opposed exterior walls 31, 31' of the elastic tube 23 (FIGS. 2 and 3) may be applied by any first member and second member structure capable of generating the appropriate opposed compressive rolling forces. For example, the compressive rolling forces could be applied by a physician's index finger and thumb rolling back and forth in a reciprocating manner. FIG. 3, in contrast, illustrates the first and second member 26, 28 as two opposed plates compressing the elastic tube 23 therebetween, and moving in opposite directions of arrows 34, 34' to produce the necessary rolling motion in the direction or arrow 35. To facilitate traction, the plate surfaces may be coated with an elastic material (rubbers, thermoplastics, and thermosets), such as silicon, natural rubber, sand paper, etc., to roll and compressively crimp the stent. Additionally, to facilitate traction, the plates may be machined or knurled to have a textured surface to increase friction between the tube and plate.

A method of crimping a stent in onto a deployment device is thus provided comprising the steps of: inserting the uncrimped stent 21 into an elastic tube 23 having an inner diameter larger than an outer diameter of the uncrimped stent 21 (FIG. 1); and compressing the elastic tube 23 until the opposed interior walls of the elastic tube 23 contact the exterior walls of the uncrimped stent 21. As viewed in FIGS. 2 and 3, the present inventive method further includes the step of compressively rolling the elastic tube 23 and the uncrimped stent 21 from an uncrimped condition to a crimped condition until the compressed stent 21 is mounted and sufficiently crimped to the deployment device 22.

To crimp the stent, the rolling step may be performed by rolling the elastic tube 23 and stent assembly 33 in reciprocating back and forth directions, or the rolling step may be performed by rolling the elastic tube and the stent assembly in one direction.

Figure 4:
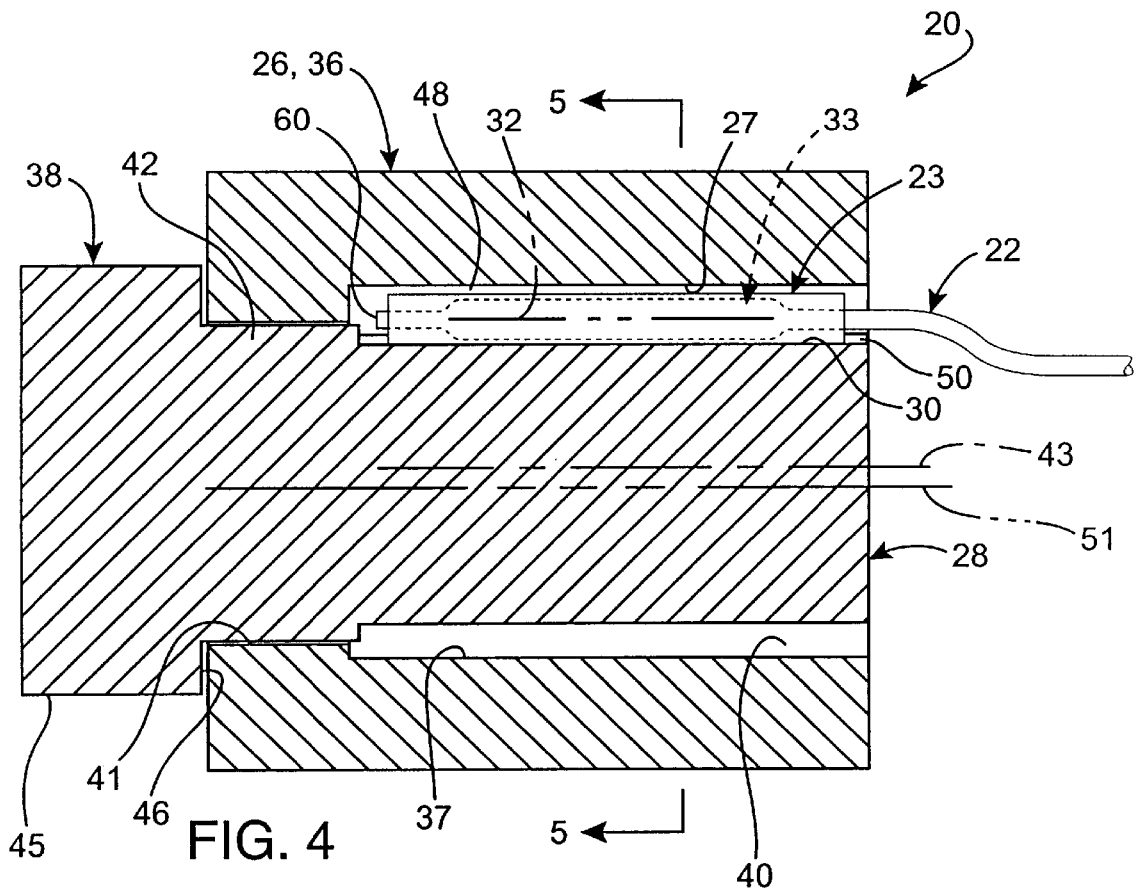
FIG. 4 is a side elevation view, in cross-section, of a second embodiment of a stent loading apparatus of the present invention employing a crimp roller.
Figure 5A:
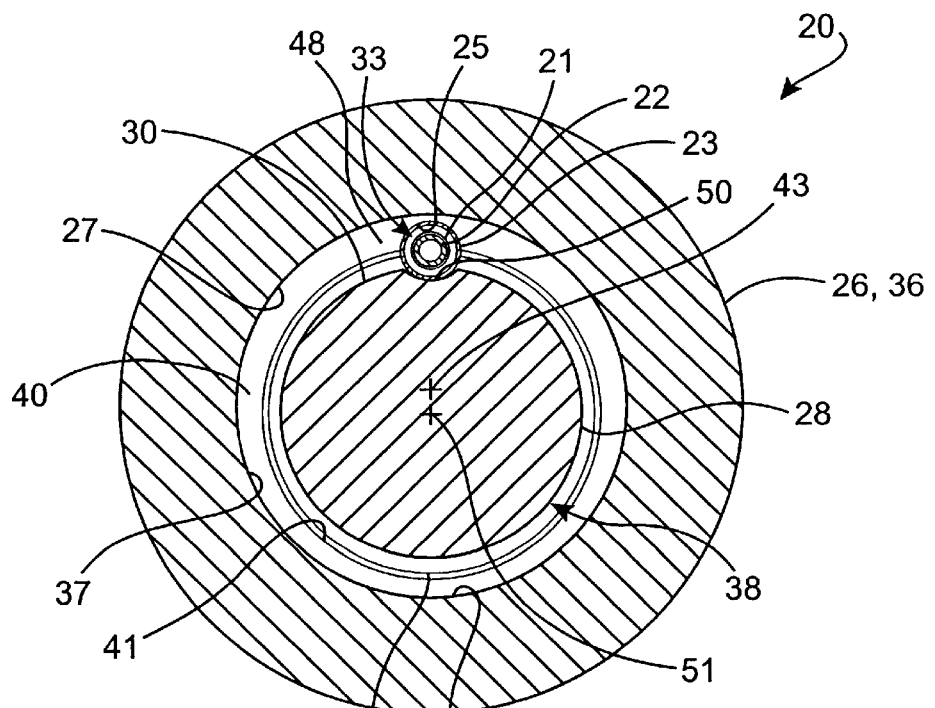
FIGS. 5A–5C are a sequence of enlarged front elevation views, in cross-section, of the second embodiment of the stent loading apparatus taken substantially along the plane of the line 5—5 in FIG. 4, and illustrating the stent loading apparatus during crimping movement between the first position and the second positions.
Figure 5B:
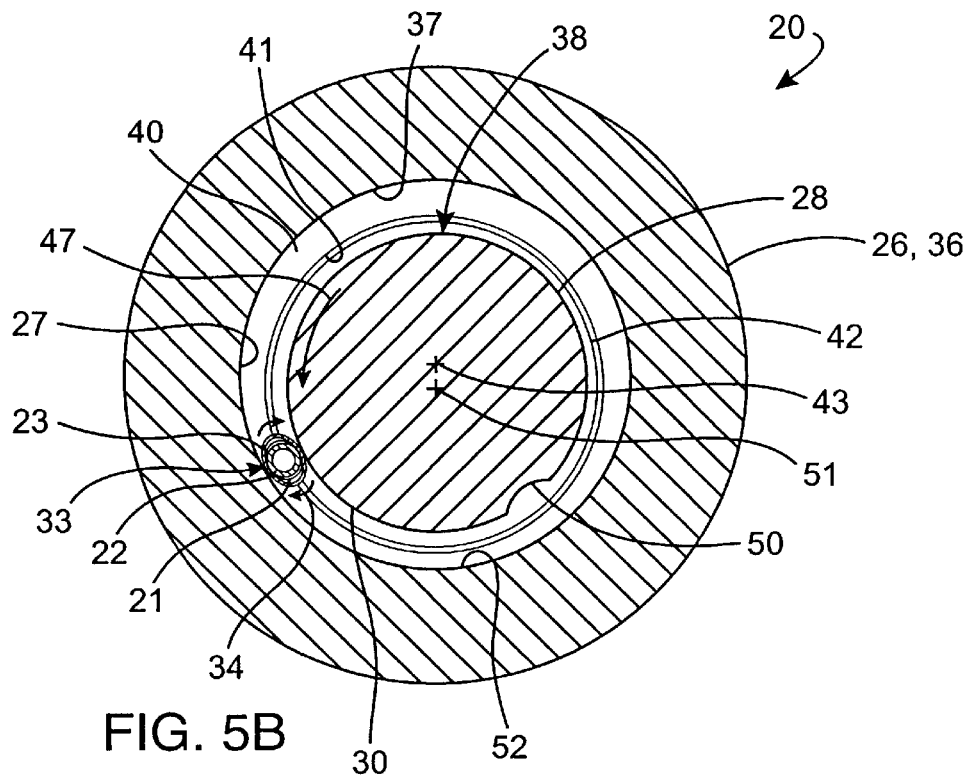
Figure 5C:
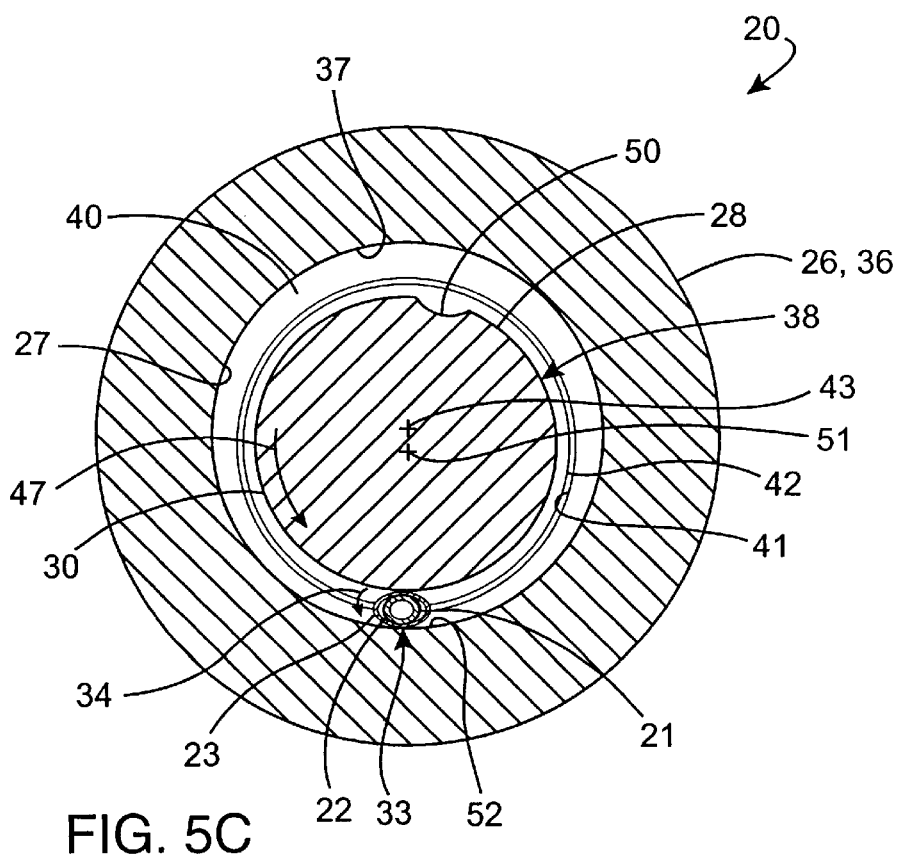

Referring now to FIGS. 4–5C, a second embodiment of the stent loading apparatus 20 of the present invention is illustrated for loading a deformable stent 21 onto a deployment device 22. In this embodiment, the first member 26 is provided a crimper body, generally designated 36, having a curvilinear first compression region, preferably wall 27, defining a bore portion 37; and a spindle member 38 having a curvilinear second compression region, preferably wall 30, extending into the bore portion 37 adjacent the first compression wall 27. Collectively, these opposed first and second compression walls define an annular gap 40 between the rotating components where the crimp is to be performed. The spindle member 38 is rotatably coupled to the crimper body 36 for relative rotation of the first compression wall 27 and the second compression wall 30 between a first position (FIGS. 4 and 5A) and a second position (FIGS. 5B and 5C). In the first position, the first compression wall 27 and the second compression wall 30 are sufficiently configured to enable receipt of the deformable stent 21 therebetween in the uncrimped position. In the second position, the opposed first and second compression walls are sufficiently configured to provide rolling radial compression of the stent 21 onto the deployment device 22.

Accordingly, the stent 21 is caused to be radially compressed and simultaneously rolled about its longitudinal axis during the relative rotational movement between first compression wall 27 and second compression wall 30. Analogous to the first embodiment, the first member is provided by the crimper body 36 defining the first compression wall 27, while the second member is provided by the spindle member 38. During relative rotational movement between the crimper body 36 and the spindle member 38, the substantially cylindrical first compression wall 27 rotates relative the cylindrical second compression wall 30 in a manner compressing and rotating the elastic tube 23 therebetween from the first position (FIGS. 4 and 5A) to the second position (FIGS. 5B and 5C) to compressively crimp the stent assembly 33.

Briefly, while the application of the present invention is primarily described and illustrated in connection with the elastic tube embodiment, it will be appreciated that this tube may be excluded so that the crimping operation is performed directly upon the stent by the opposed first and second compression walls 27, 30. In this arrangement, however, the protective buffer provided by the elastic tube as well as the enhanced traction between the uncrimped stent 21 and the compression walls is eliminated.

Crimper body 36 is preferably composed of a rigid material or the like having low level radiation shielding properties to function as a radiation shield when radioactive stents are being crimped. This material is preferably provided by an acrylic, leaded acrylic, glass, leaded glass, polycarbonate, stainless steel and lead, or the like of sufficient thickness to provide shielding properties. For example, for an acrylic material to shield beta radiation, the thickness of first compression wall is preferably about 0.2 inches to about 0.5 inches. Such radioactive shielding qualities will be described in greater detail below.

FIGS. 4 and 5A illustrate that crimper body 36 provides an elongated bore portion 37 extending longitudinally into an interior portion of the body from a proximal end thereof. At the distal end of crimper body 36 is a substantially cylindrical bearing port 41 extending into and communicating with bore portion 37. In this configuration, the second member 28 is provided by a crimp roller 28 of spindle member 38 which extends through port 41 and into bore portion 37, to position the second compression wall 30 of the crimp roller adjacent and opposed the first compression wall 27.

The diameter of bearing port 41 is sized and dimensioned for rotational receipt of a bearing portion 42 of spindle member 38 therein to rotatably couple the spindle member to the crimper body. This rotational coupling about the respective longitudinal axis is preferably an interference fit (i.e., sufficiently tight to substantially reduce substantial lateral movement, while sufficiently loose to enable relative rotational motion about the longitudinal axis). A longitudinal axis of port 41 is substantially parallel to a longitudinal axis 43 of the bore portion 37 so that upon rotational motion of the spindle member 38 the crimper body 36, the gap distance between the second compression wall 30 and the first compression wall 27 radially therealong remains substantially constant for a cylindrical crimp roller. Moreover, a substantially uniform radial compressive rolling force is urged upon the stent 21 longitudinally therealong as the stent rolls between the first and second positions.

At a distal end of spindle member 38 is a crimper knob 45 extending outside of crimper body 36 to provide manual access for rotative manipulation of the crimp roller 28 relative the first compression wall 27. The diameter of knob 45 is preferably greater than that of bearing port 41 so that a lip portion 46 of knob 45 functions as a stop to limit the depth of insertion of the crimp roller 28 into bore portion 37. The crimper knob 45 is preferably rigidly coupled to crimp roller 28 such that the rotation of the knob produces a 1:1 ratio rotation of the crimp roller. It will be appreciated, of course, that a gear assembly or the like could be provided therebetween to alter the rotation ratio without departing from the true spirit and nature of the present invention. Moreover, the relative rotation motion between the spindle member and the crimper body may be driven by any conventional means as well.

As best viewed in FIGS. 5A–5C, rotation of the spindle member 38 (in the direction of arrow 47 in these examples) causes the uncrimped stent assembly to be rollingly radially compressed or pinched between first compression wall 27 and the opposed second compression wall 30. As the crimp roller 28 is rotated from the first position (FIG. 5A) to, the second positions of FIGS. 5B or 5C, for example, the stent assembly is caused to move in the annular gap 40 formed between the crimper body and the rotate spindle member in the direction of arrow 47, as well. Hence, not only is stent device properly uniformly compressed, at a substantially predetermined pressure between the first compression wall and the second compression wall, but the same is caused to be supportively rolled therebetween about its longitudinal axis for a uniformly distributed crimp as well.

In this arrangement, access to the annular gap 40 of stent loading apparatus 20 is provided through an annular opening formed between the proximal end of crimp roller 28 and the proximal end of crimper body 36. In the first position (FIG. 5A), the first compression wall 27 of crimper body 36 and the second compression wall 30 of crimp roller 28 cooperate to form an insertion cavity 48 therebetween sufficiently sized to enable longitudinal sliding insertion of the stent assembly 33 and/or the elastic tube 23 prior to the crimping. Thus, the annular gap 40 between the first and second compression walls will be larger at the first position than at the crimping portions of the second positions. This increased space promotes uninterfered longitudinal insertion of the uncrimped stent assembly into the passage 25 of the elastic tube 23.

One technique to form insertion cavity 48 between the crimper body 36 and the crimp roller 28 is to provide a longitudinally extending groove portion 50 in either or both of the first compression wall 27 and the second compression wall 30 at the first position. As shown in FIGS. 5A–5C, semi-circular groove portion 50 is preferably formed in the second compression wall 30 of a sufficient depth to create the necessary space. In some instances, insertion cavity 48 may be dimensioned to provide a continuous interference fit of elastic tube with the compressing walls so that the tube is to always caused to roll (even out of the groove portion 50) upon relative rotation between the spindle member 38 and the crimper body 36.

Another technique to define insertion cavity 48 at the first position is to off-set the rotational longitudinal axis 51 of the spindle member from the longitudinal axis 43 of bore portion 37. In this arrangement, therefore, the respective longitudinal axes are not co-axial. This is preferably performed by proportionally off-setting the longitudinal axis 51 of the bearing port 41 from that of the bore portion 37 (FIGS. 5A–5C). Although the respective axes remain substantially parallel, the substantially cylindrical second compression wall 30 would thus not be concentric with the substantially cylindrical first compression wall 27. FIG. 5A therefore illustrates that the insertion cavity 48 is positioned at an upper apex portion of the annular gap 40 between the off-set components. Moreover, if a combination of the off-set components and a longitudinal groove portion 50 are employed, such as in this embodiment, the first position will be formed when the groove portion 50 is aligned at the upper apex portion of the annular gap 40 (FIG. 5A).

Once the uncrimped stent assembly 33 and the elastic tube 23 are positioned between the crimp roller 28 and the crimper body 36, in the first position, the knob 45 may be manually or automatically rotated relative crimper body 36. This relative rotation of the crimp roller 28 and the first compression wall 27 causes the interference fit elastic tube 23 to roll out of groove portion 50. Continued relative rotation between the spindle member and the crimper body urges the stent assembly toward the second position, as best viewed in FIGS. 5B and 5C. The interference fit between the elastic tube 23 in the annular gap 40 further operates to maintain the elastic tube substantially longitudinally in the annular gap 40 by applying equal pressure along the length of the tube. This aspect of the rolling compressive crimp is critical since skewing of the stent assembly 33 in the annular gap not only causes a non-uniform distribution of compression forces on the stent, but may further potentially damage the whole stent assembly.

Due to the off-set nature of the crimp roller 28, the degree of the crimp may be adjusted as the stent assembly rollingly progresses toward the lower apex portion 52 of the annular gap 40. Essentially, the crimp becomes increasingly and incrementally tighter as the gap distance between the first compression wall 27 and the second compression wall 30 progressively narrows towards the lower apex portion 52. It will be appreciated of course that the tightest crimp is available by compressively rolling the stent assembly 33 through the lower apex portion 52 where the distance between the first compression wall and the second compression wall is the narrowest (FIG. 5C).

Accordingly, the tightness of the stent may be adjusted and controlled by limiting the progression of the stent assembly through the annular gap. Moveable stop members or indices along the respective components, both of which are not shown, may be included to limit the relative rotation of the spindle member or indicate to the operator the compression of the crimp. In this manner, overcrimping of the stent device can be substantially controlled.

This same concept may be achieved by altering either the bore portion or the crimp roller to have respective transverse cross-sectional dimensions which are slightly parabolic in shape or the like (not shown). Collectively the gap distance between the first compression wall and the second compression wall would vary to adjust the crimp pressure. In this arrangement, thus, the longitudinal axis of the crimp roller could still be co-axial with that of the bore portion.

Once the stent 21 is properly crimped onto the balloon catheter 22, the spindle member 38 may be rotated in an opposite direction (opposite arrow 47) to release the compressive rolling forces generated by the opposed compression walls 27, 30. Once the reduction of compressive forces is sufficient to slideably release the crimped stent assembly, the same may be withdrawn from the annular gap 40 and the passage of elastic tube 23. To remove the elastic tube 23, the tube may have to be moved to the first position due to the interference fit. Further, it will be appreciated that when the tightest crimp available is necessary, in this configuration, once the stent assembly 33 has reached the lower apex portion 52 of the annular gap 40, the stent assembly may be released by continuing the relative rotation in the same direction. In contrast, when a maximum crimp is undesirable, compressive release of the stent assembly can only be achieved by reversing the relative rotational direction of the spindle member 38.

Turning now to FIGS. 6A–7C, a third embodiment of stent loading apparatus of the present invention is illustrated which is particularly suitable for loading a radioisotope emitting stent 21 onto a deployment device 22. In this third embodiment, a crimping mechanism 53 is adapted to crimp the radioactive stent 21 onto the deployment device 22. A shielded crimper body 36 provides a bore portion 37 formed for receipt of the radioactive stent and the crimping mechanism 53 therein. The crimper body 36 and the crimping mechanism 53 cooperate to substantially prevent the passage of radiation from the bore portion during crimping of the radioactive stent 21 by the crimping mechanism.

In accordance with this embodiment of the present invention, a physician or lab technician will be substantially shielded from radiation emitted from the radioactive stents during the crimping operation. This is primarily performed by enclosing the crimping mechanism inside the bore portion of the crimper body, and then further shielding the remaining communication orifices or the like extending therein to substantially prevent the passage of radiation from the bore portion.

Figure 6A:
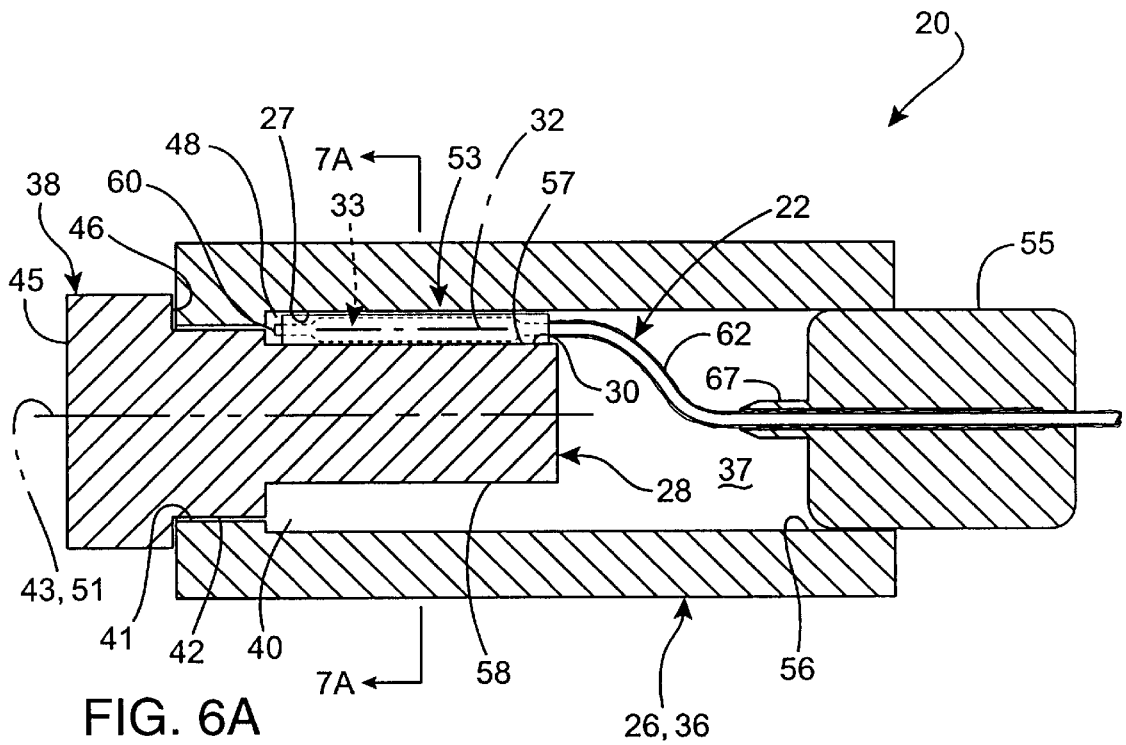
FIGS. 6A and 6B are a sequence of side elevation views, in cross-section, of a third embodiment of a stent loading apparatus of the present invention mating with a radiation shield device for a radioactive stent.
Figure 6B:
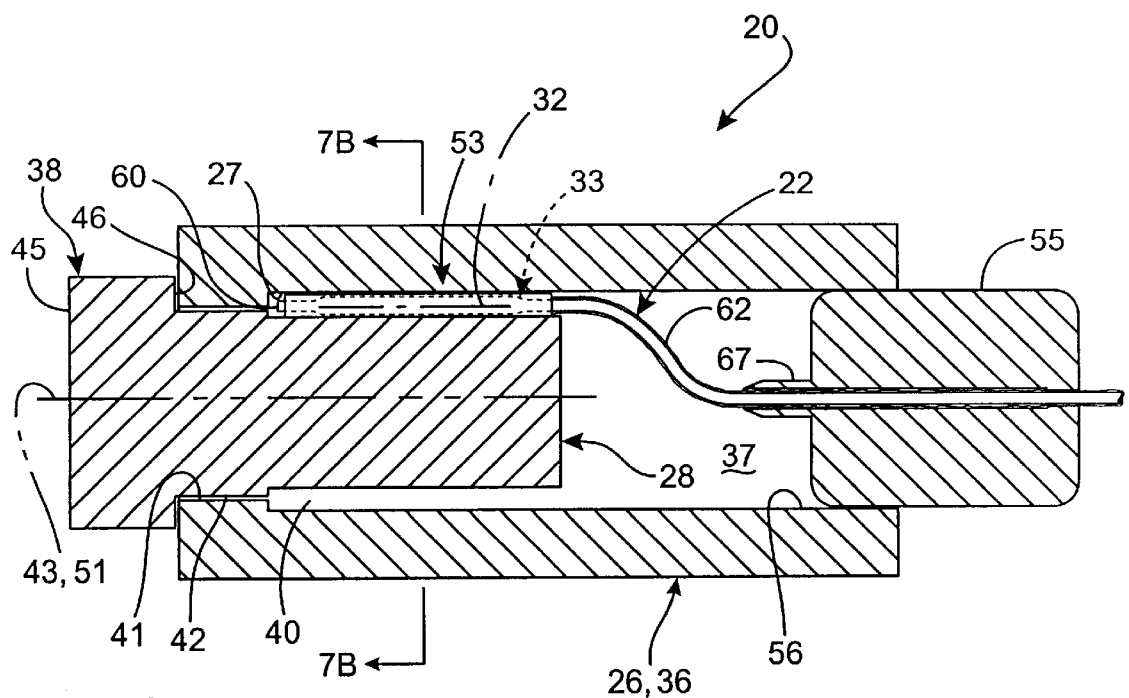

As best viewed in FIGS. 6A and 6B, the stent loading apparatus 20 preferably mates and cooperates with a radioactive stent radiation shield, generally designated 55, which may be employed for the safe transportation of a radioactive stent or stent assembly. Collectively, the stent loading assembly and the radiation shield provide an operational crimping assembly which substantially shields and protects the operator from radioactive particles emitted by the radioactive stent during the crimping operation.

The radiation shield 55 may be provided by any conventional shielded transport mechanism which effectively shields the operator from the radioactive stent or radioactive stent assembly during transport. One such radiation shield, for example, is provided by U.S. Pat. No. 5,605,530 entitled "System for Safe Implantation of Radioisotope Stents" which is incorporated by reference in its entirety.

As above-mentioned, crimper body 36 is preferably a sufficient thickness and composed of an appropriate material to provide radiation shielding. Similarly, it will be appreciated, that the spindle member 38 and the radiation shield 55 provide like radioactive protection as well.

To accommodate the cylindrical radiation shield 55, the proximal end of crimper body 36 extends substantially beyond the proximal end of spindle member 38. An access opening 56 into bore portion 37 is formed and dimensioned for longitudinal sliding receipt of radiation shield therein. Hence, the transverse cross-sectional dimension of the access opening 56 is configured to slideably receive the transverse cross-sectional dimension of the radiation shield 55. This interference fit should be sufficiently tight to substantially prevent the passage of radiation from the creases therebetween, while being sufficiently loose to enable selective sliding separation of the components.

The access opening 56 may be slightly tapered inwardly toward an interior of the bore portion to limit the insertion of the radiation shield therein. Further, it will be understood that the distal end of the radiation shield should be sufficiently spaced apart from the proximal end of crimp roller 28 to enable the stent assembly to be positioned in the annular gap 40 of the stent loading apparatus without damaging the stem of the balloon catheter 22. In the preferred form this distance should be in the range of at least about one (1) inch to about four (4) inches.

Referring back to FIGS. 7A–7C, another technique is employed to form the insertion cavity 48 at the first position. The second compression wall 30 may include a variation of the longitudinal groove portion 50 which further incorporates a recessed wall portion 57 thereof to broadening size of the insertion cavity 48. In combination with the longitudinal groove portion 50, recessed wall portion 57 further facilitates alignment and the sliding insertion of the stent assembly and/or the elastic tube 23 into the annular gap 40 at the first position (FIG. 7A) by significantly increasing the size of the insertion cavity.

Figure 7A:
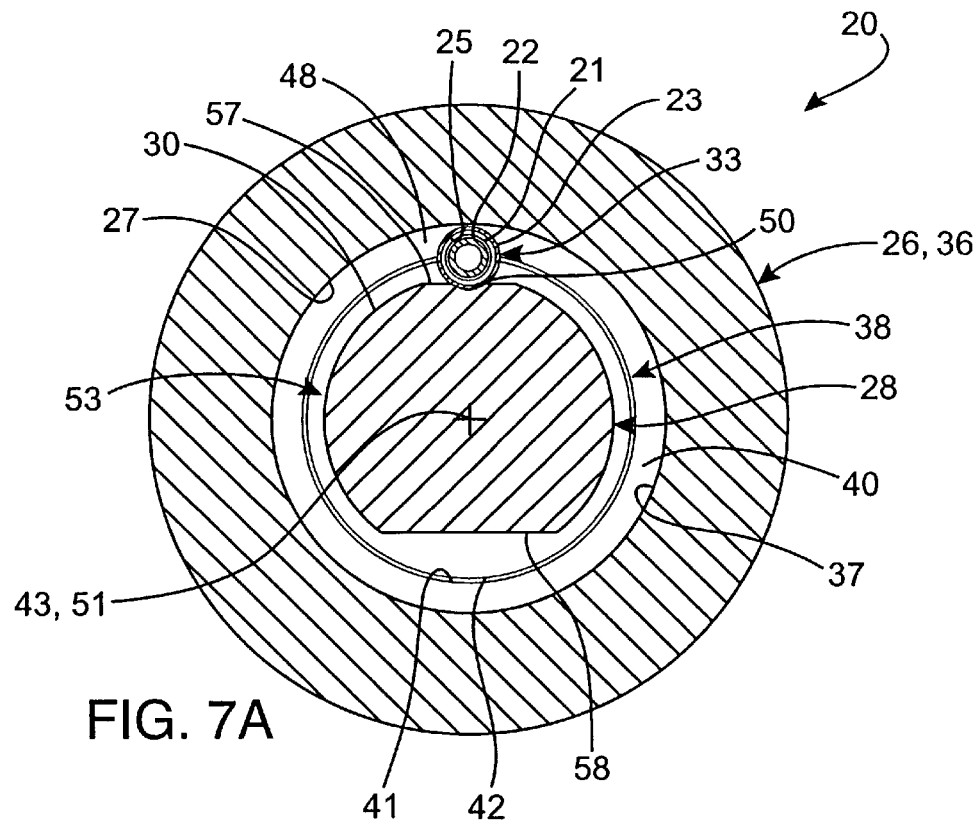
FIGS. 7A–7C are a sequence of enlarged front elevation views, in cross-section, of the third embodiment of the stent loading apparatus taken substantially along the plane of the line 7—7 in FIGS. 6A and 6B, and illustrating the stent loading apparatus during crimping movement between the first position and the second positions.
Figure 7B:
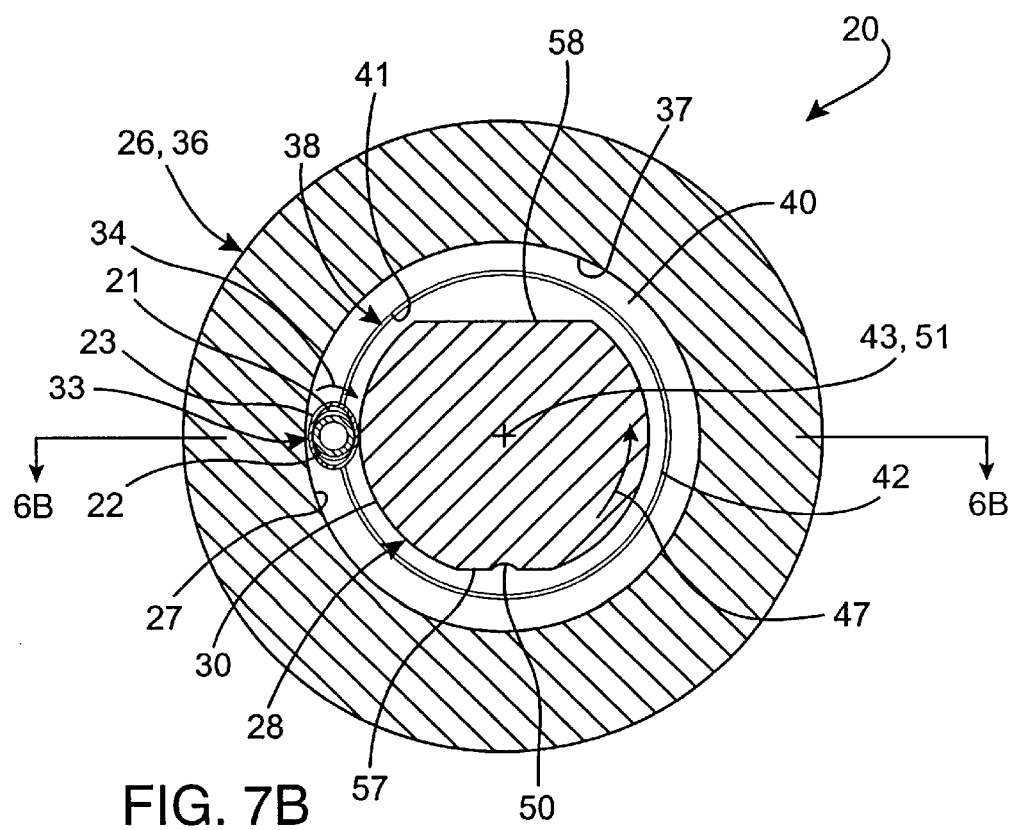

Similar to the other crimp roller embodiments, upon relative rotational motion between the spindle member 38 and the crimper body 36, the elastic tube 23 is caused to roll out of groove portion 50 for rolling compression at the second positions of the annular gap 40 (FIG. 7B). In this configuration, the longitudinal axis 51 of the crimp roller 28 is illustrated as substantially co-axial with the longitudinal axis 43 of the bore portion 37. Moreover, since the transverse cross-sectional dimensions of crimp roller 28 and the bore portion 37 are substantially cylindrical, the components are oriented substantially concentric. The gap distance between the first and second compression walls 27, 30, therefore, is substantially constant circumferentially along the second positions which provides a substantially equal compressive rolling forces.

Figure 7C:
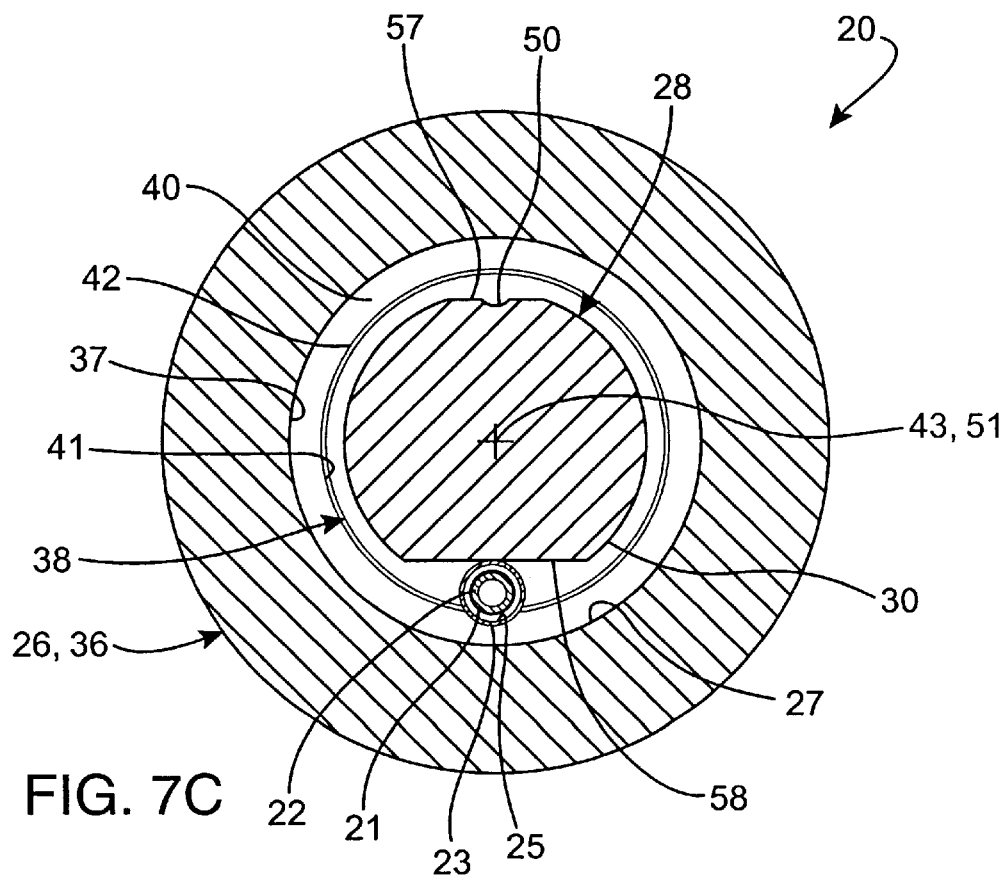

Once the stent 21 is properly crimped to balloon catheter 22, the spindle member 38 may be moved to a removal position which facilitates removal of the stent assembly 33 and/or elastic tube 23 from the annular gap 40. As shown in FIG. 7C, crimp roller 28 includes a second recessed wall portion 58 at an opposite side of first recessed wall portion 57 which cooperates with the first compression wall 27 to substantially increase the space therebetween. Upon movement to this removal position, the stent assembly 33 may be easily withdrawn from the annular gap 40 and is retracted into the radiation shield 55. Subsequently, the radiation shield may be withdrawn from the access opening 56 of the bore portion 37.

Figure 8:
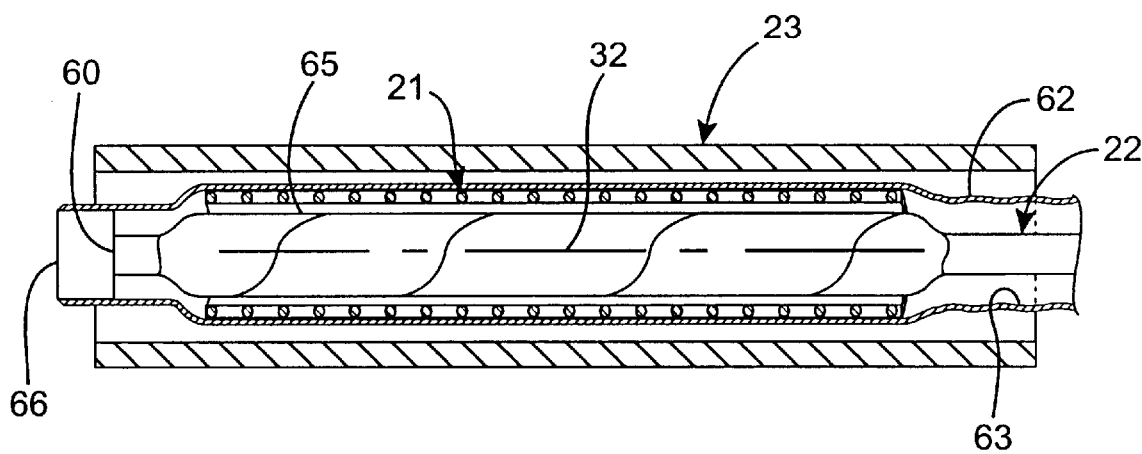
FIG. 8 is an enlarged, fragmentary, side elevation view, in cross-section, of an elastic tube stent loading embodiment of FIG. 1 employing a shrink fit tube to facilitate positioning of the uncrimped stent onto the balloon catheter.

To facilitate positioning and alignment of the distal tip 60 of balloon catheter 22 through the uncrimped stent 21, a shrink tube assembly 61 (FIG. 8) may be provided having a shrink tube 62 which is radially shrunk fit peripherally around the uncrimped stent 21. As best illustrated in FIG. 8, an uncrimped elongated stent 21 is provided having an uncrimped diameter suitable for sliding receipt on the balloon of the balloon catheter. The shrink tube 62 includes a passage 63 having an unshrunk diameter, in an unshrunk condition (not shown), larger than the uncrimped diameter of the stent 21 for sliding receipt of the stent into the shrink tube passage 63. Upon heat shrinking the shrink tube 62 in a conventional manner to a shrunk condition (FIG. 8), the resulting shrunk diameter of the passage 63 is smaller than the uncrimped diameter to secure the shrink tube 62 substantially peripherally around the stent 21 for support thereof, and to facilitate positioning and alignment of the deployment device 22 relative the uncrimped stent.

Accordingly, in the unshrunk condition, the shrink tube 62 must be sufficiently sized diametrically to enable sliding receipt of the uncrimped stent 21 therethrough; while in the shrunk condition, the shrink tube 62 must be sufficiently reduced in diameter so that the uncrimped stent may be secured and maintained in place longitudinally along the passage of the shrink tube. Upon heat shrinking of the shrink tube 62, the portions peripherally surrounding the uncrimped stent will come to rest upon the exterior surface thereof, while the portions of the shrunk tube extending beyond the proximal and distal ends of the stent will continue to shrink in diameter. Thus., as shown in FIG. 8, the proximal and distal portions of the shrink tube which are not radially supported by the uncrimped stent 21 will continue to shrink to a diameter smaller than the outer diameter of the uncrimped stent. It is these portions of the shrink tube 62 just proximal and distal to the stent ends which longitudinally secure the stent relative the shrink tube.

This securing of the uncrimped stent 21 relative the shrink tube 62 enables the balloon catheter 22 to be slideably positioned through the passage 63 thereof until the balloon 65 is properly positioned in the stent prior to crimping. Moreover, this mounting arrangement further facilitates maintenance of the alignment between the balloon catheter 22 and the stent 21 during positioning of the stent assembly 33 in the elastic tube 23 at the first position (FIG. 6A) and during the crimping procedure (FIG. 6B).

For example, for a 0.050" inside diameter×0.060" outside diameter uncrimped stent, the unshrunk diameter of the passage 63 of a shrink tube may range from about 0.060" inner diameter to about 0.065" inner diameter, while in the shrunk condition, the passage may range from about 0.045" inner diameter to about 0.050" inner diameter. The shrink fit tubing may be provided by any conventional tubing material which shrinks to the proper diametric dimensions. Typically, the composition of these tube is provided by a thermoplastic such as PET, or the like. Further, the thickness of the tubing in the shrunk condition is preferably about 0.001" to about 0.005" which is sufficiently thick to avoid damage thereof when the balloon catheter is being positioned through the passage 63.

To further promote alignment of the secured uncrimped stent 21 with the balloon catheter 22, a plug member 66 (FIG. 8) may be provided which is positioned at the distal end of the tube thereof. This plug member, preferably composed of a thermoplastic or thermoset, functions a stop structure for the balloon catheter to abut against when the catheter is being positioned through the shrink tube in the shrunk condition. Once the distal tip portion 60 of the deployment device 22 contacts a proximal end of plug member 66, the expandable balloon 65 will be properly positioned and aligned relative the uncrimped stent. Therefore, during positioning of the uncrimped stent 21 in shrink tube passage 63, the uncrimped stent must be positioned a predetermined distance from the proximal end of the plug member 66.

As shown in FIGS. 6A and 6B, on the proximal side of the stent 21, the shrink tube 62 preferably extends from the stent to the radiation shield 55. The proximal end of the shrink tube 62 can either terminate at the proboscis 67 of the radiation shield, the interior portion of the passage 63 the shrink tube 62 through the shield, or even extend all the way through the shield. In this arrangement, the distal tip 60 of the balloon catheter may be positioned through the radiation shield 55 and into the shrink tube passage 63 until the distal tip 60 abuts the plug member 66. At this orientation, the balloon of the balloon catheter will be aligned and positioned in the uncrimped stent when the stent and shrink fit tube are positioned in the elastic tube at the first position of the stent loading apparatus.

Once the stent assembly 33 has passed through the second position of the annular gap, the crimped stent will preferably be of a diameter smaller than the passage 63 of the shrink tube 62 in the shrunk condition. This dimension enables the stent assembly 33 to be easily withdrawn from the shrink tube without adverse consequences.

While the shrink tube configuration is only illustrated and described in connection with the embodiments of FIGS. 6 and 7, it will be appreciated that this application may be applied to any of the embodiments without departing from the true spirit and scope of the present invention. Moreover, in another aspect of this embodiment of the present invention, a securing tube (not shown) may be provided in place of the shrink tube which is comprised of a thermally deformable material. In this arrangement, the securing tube may be thermally deformed just at the portions peripherally around the proximal and distal ends of the uncrimped stents to longitudinally imprison the stent therein when in the uncrimped condition. Accordingly, while the securing tube does is wholly shrunk peripherally around the uncrimped stent, the distal end and proximal portions of the tube communicating with the distal and proximal ends of the tube are sufficiently deformed therearound in a manner securing the stent longitudinally along the securing tube.

Turning now to FIGS. 9–11B, a fourth embodiment of the stent loading of the present invention is illustrated having a planetary gear assembly, generally designated 68, which enables smooth and accurate rotation of the spindle member 38 relative the crimper body 36. This gear assembly 68 further facilitates rolling transport of the stent assembly, the catheter, the crimp tube and the radiation shield about the annular gap 40 at a substantially similar rate and distance, and in a longitudinal orientation between the first and second compression walls.

Figure 9:
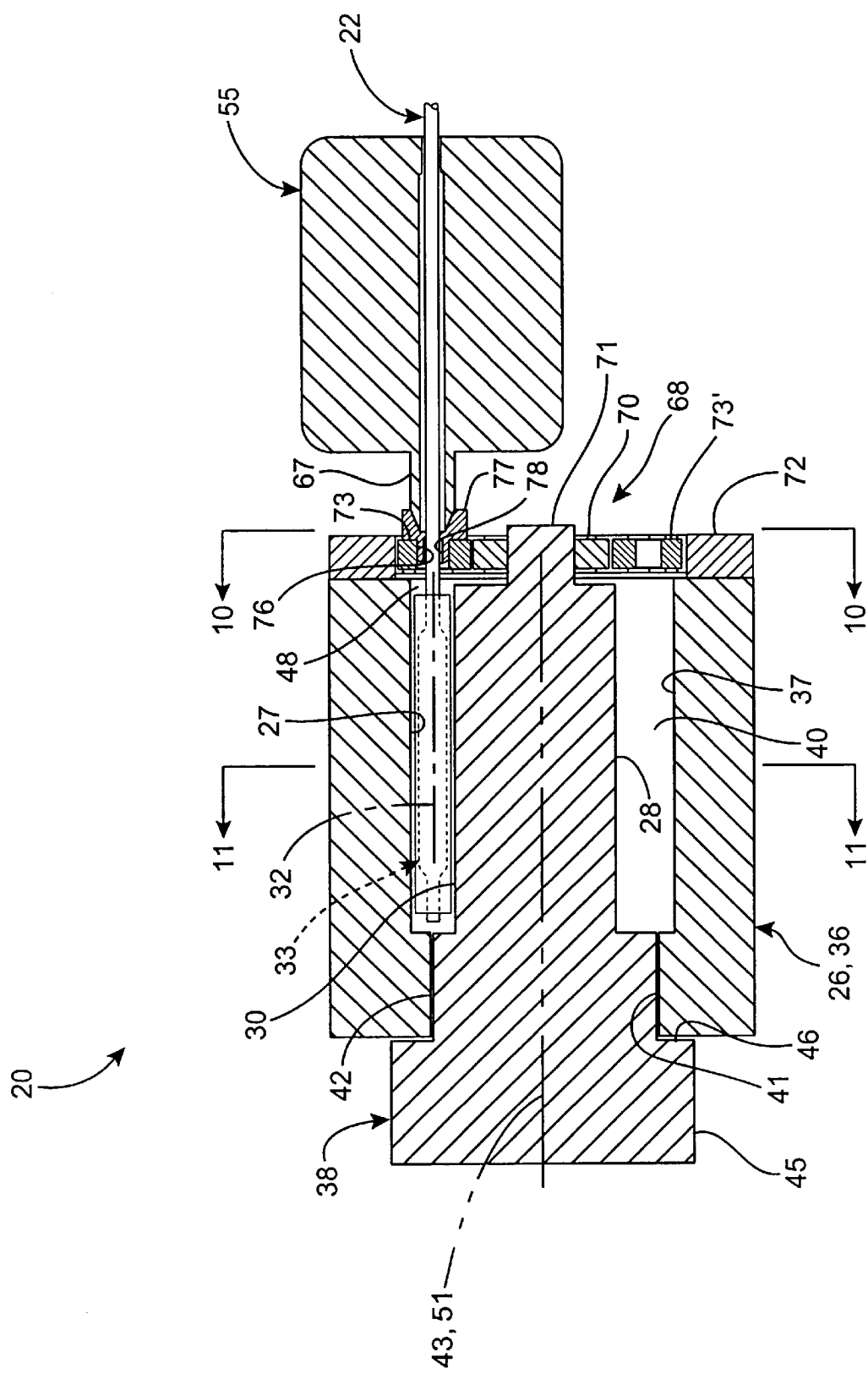
FIG. 9 is a side elevation view, in cross-section, of a fourth embodiment of a stent loading apparatus of the present invention including a gear assembly.
Figure 11A:
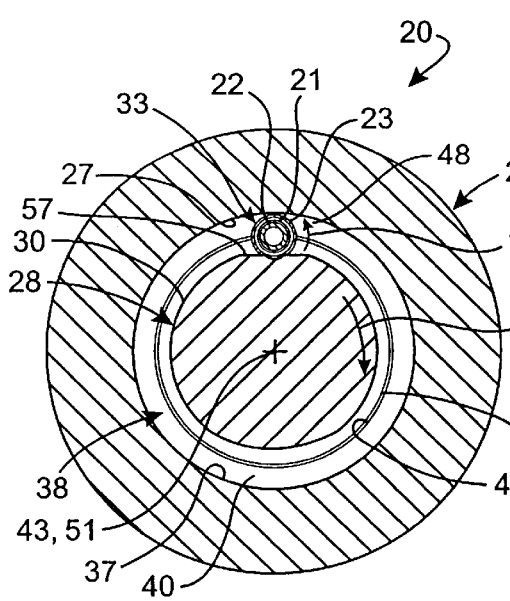
FIGS. 11A and 11B are a sequence of enlarged front elevation views, in cross-section, of the fourth embodiment of the stent loading apparatus taken substantially along the plane of the line 11—11 in FIG. 9, and illustrating the crimp roller engaging the stent during crimping movement between the first position and the second positions.
Figure 10A:
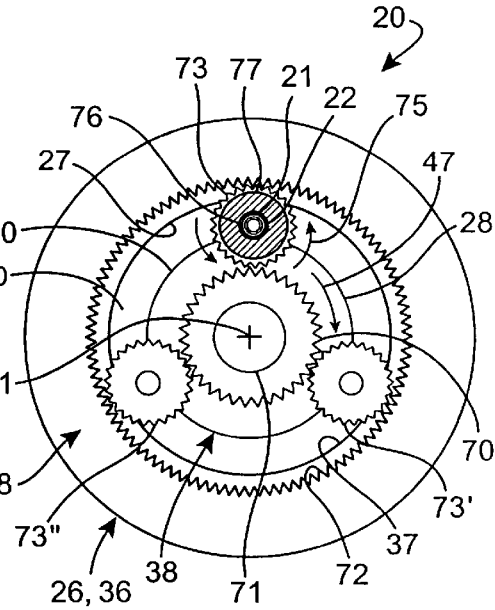
FIGS. 10A and 10B are a sequence of enlarged front elevation views, in cross-section, of the fourth embodiment of the stent loading apparatus taken substantially along the plane of the line 10—10 in FIG. 9, and illustrating the gear assembly during crimping movement between the first position and the second positions.
Figure 11B:
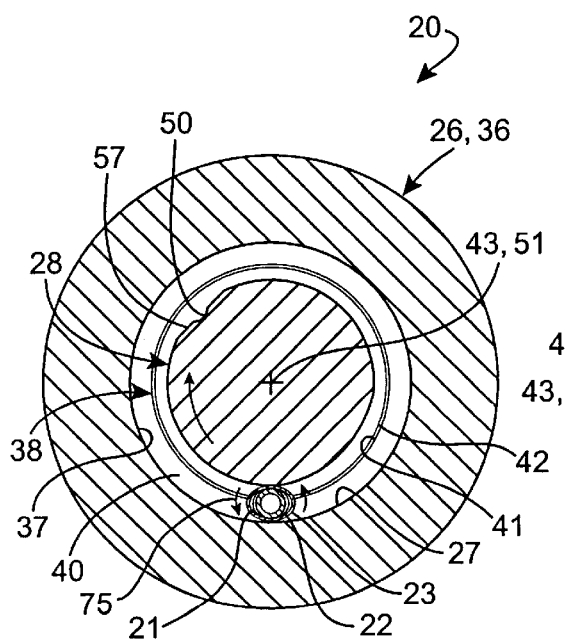
Figure 10B:
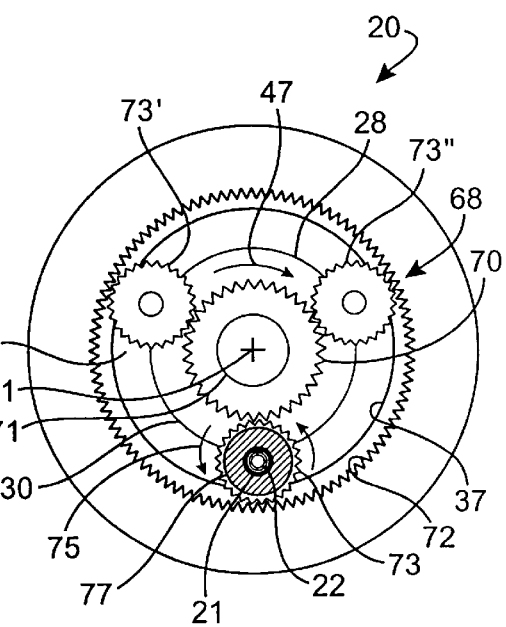

As shown in FIGS. 11A and 11B gear assembly 68 is configured to cooperate with the crimper body 36, the spindle member 38 and the deployment device 22 to provide rolling support for the stent assembly 33 between the first position (FIGS. 9, 10A and 11A) and the second position (FIGS. 10B and 11B). The planetary gear assembly 68 preferably includes a drive gear 70 fixedly coupled to the proximal end of crimp roller 28 through post portion 71. Positioned circumferentially about drive gear 70 is an internal ring gear 72 having internally facing teeth. This ring gear 72 is preferably fixedly mounted to the proximal end of crimper body 36 proximate the access opening into the annular gap 40. Gear assembly 68 further includes at least one spur gear 73 driveably meshed between the drive gear 70 and the internal ring gear 72. As shown in FIGS. 10A and 10B, the planetary gear assembly 68 is configured to rotatably position the spur gear 73 along the access opening of the annular gap 40. In accordance with this embodiment of the present invention, the deployment device 22 is coupled to the spur gear as it moves around the annular gap 40 to facilitate movement of the stent assembly 33 between the first position and the second position.

Upon driving rotation of spindle member 38 in the direction of arrow 47 (FIGS. 11A and 11B) and about the spindle longitudinal axis, the drive gear 70 causes the rotation of spur gear 73 in the rotational direction of arrow 75 about the spur gear longitudinal axis. Due to the spur gear's cooperation with the internal ring gear 72 affixed to crimper body 36, the spur gear 73 is caused to move about the annular gap in the direction of arrow 47. Thus, as the spur gear 73 is moved about the annular gap 40, the stent assembly 33 coupled thereto is also moved around the annular gap simultaneously (FIGS. 10A and 10B) in a rolling compressive manner to crimp the stent between the first compression wall 27 and the second compression wall 30.

To enhance symmetry and alignment, a second spur gear 73' and a third spur gear 73" spaced apart from the first spur gear 73 may be provided between the drive gear 70 and the ring gear 72. These spur gears, of course, travel about the annular gap at the same pace as the first spur gear 73 so as not to contact one another. To retain the spur gears in place, a mounting ring (not shown) may be included at the proximal end of the ring gear. As shown in FIGS. 10A and 10B, the mounting ring would position the spur gears against the proximal ends of the crimper body 36 and the crimp roller portions defining the access opening into the annular gap 40.

As best viewed in FIG. 9, first spur gear 73 includes an aperture 76 extending therethrough for access into the annular gap 40. This aperture 76 is sized to enable the passage of the stent assembly 33 therethrough for positioning into the elastic tube 23 in the first position (FIG. 10A). Preferably, a luer lock device 77 is provided which includes an extension configured for insertion into the aperture 76 of the first spur gear 73. Luer lock device 77 further provides a hole 78 therethrough formed and dimensioned for sliding receipt of the stent assembly. Hence, as the first spur gear 73 is rotatably urged about the annular gap 40, the luer lock device 77 further urges the stem of the deployment device 22 simultaneously about the annular gap.

The luer lock device is further formed to mate with the proboscis 67 of a radiation shield 55 so that once crimped, the crimped stent assembly may be withdrawn from the annular gap, through the luer lock hole 78 and immediately into the radiation shield. Moreover, with minor alterations, this embodiment may sufficiently shield an operator from the passage of radiation from the annular gap 40.

Figure 14A:
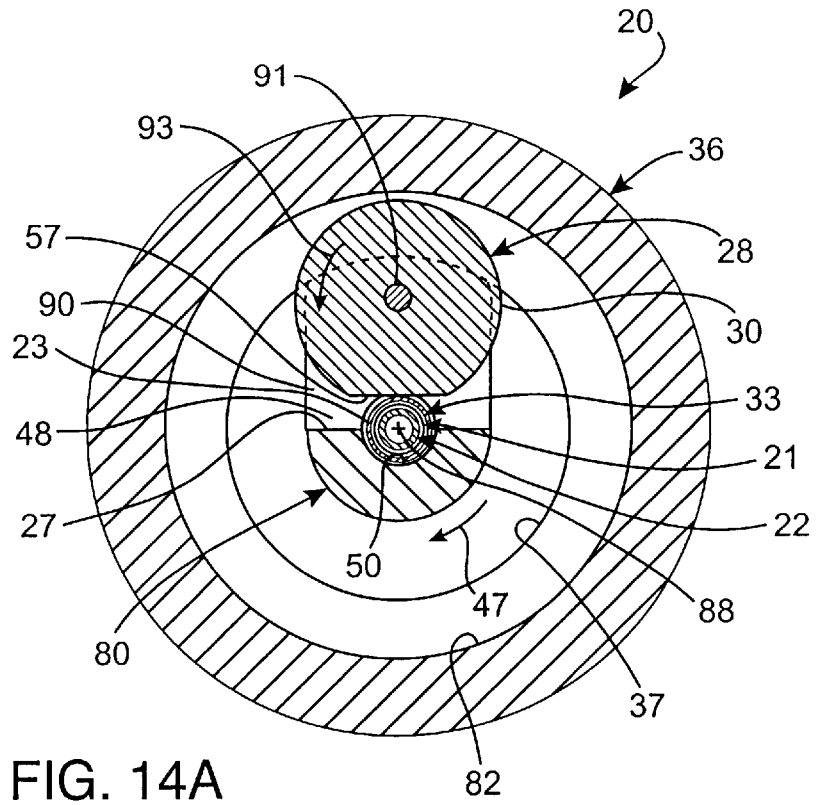
FIGS. 14A and 14B are a sequence of enlarged front elevation views, in cross-section, of the fifth embodiment of the stent loading apparatus taken substantially along the plane of the line 14—14 in FIG. 12, and illustrating the crimp roller engaging the stent during crimping movement between the first position and the second positions.
Figure 14B:
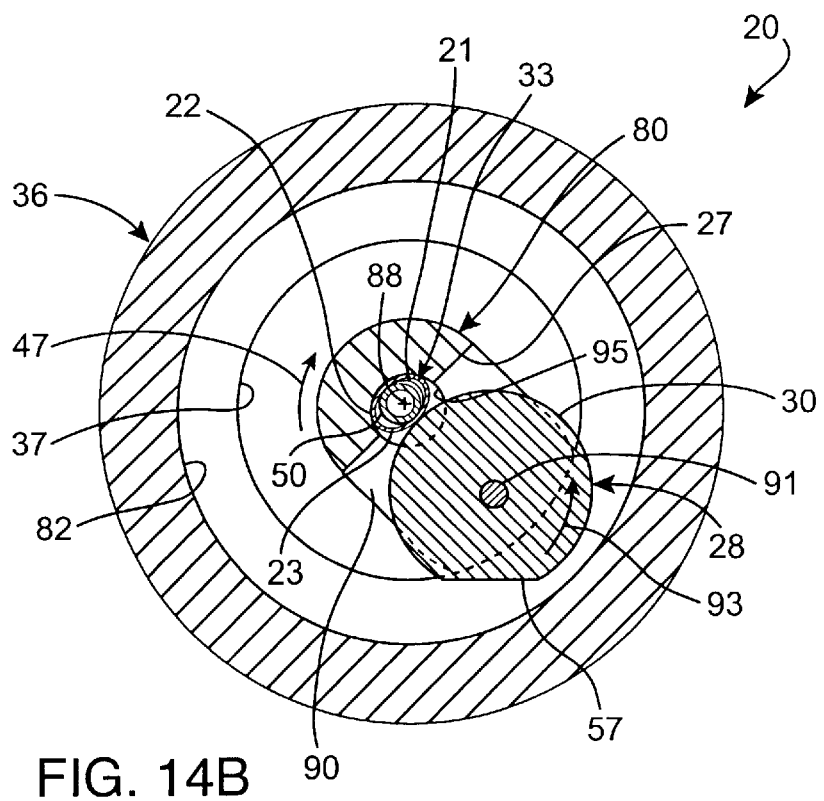

FIGS. 12–14B illustrate a fifth embodiment of the stent loading apparatus 20 of the present invention which includes a roller housing, generally designated 80, having a first compression wall 27, and a crimp roller 28 rotatably coupled to the roller housing 80. The crimp roller 28 further includes a substantially cylindrical second compression wall 30 positioned adjacent and substantially parallel to the first compression wall 27. A drive mechanism 81 is coupled between the crimp roller 28 and the roller housing 80 for relative rotation of the second compression wall 30 and the first compression wall 27 between a first position (FIGS. 12, 13A and 14A) and a second position (FIGS. 13B and 14B). In the first position, the first compression wall 27 and the second compression wall 30 are sufficiently spaced to enable receipt of the deformable stent 21 therebetween. In the second position, the opposed first and second compression walls are sufficiently spaced to roll and radially compress the stent 21 onto the deployment device 22.

Similar to the previous embodiment, while the stent assembly 33 (i.e., the stent and the balloon of the balloon catheter combination) may be directly crimped in the stent loading apparatus 20, the uncrimped stent assembly 33 is preferably positioned in an elastic tube 23 which facilitates rolling between the opposed compression walls and provides a protective barrier against damage thereof. Thus, the elastic tube 23 is positioned for compressive rolling contact between the first compression wall 27 and the second compression wall 30.

In contrast to the previous crimp roller embodiments, however, is that this crimping arrangement provides a rolling compressive crimp which maintains the elastic tube 23 and stent assembly 33 in a relatively stationary condition. As best illustrated in FIGS. 14A and 14B, the crimp roller 28 and the roller housing 80 are configured to roll around the elastic tube 23 and the stent assembly 33 to compress the same between the respective first and second compression walls. Accordingly, the stent assembly 33 will not be twisted around the stem of the balloon catheter during the rolling compression between the first and second positions.

In the preferred embodiment a crimper body 36 is provided which functions to shield the operator from the radioactive stent during the crimping procedure. Crimper body 36 is rotatably coupled to the roller housing 80 through drive mechanism 81 such that upon relative rotation between the crimper body 36 and the roller housing, the crimp roller 28 is caused to compressively roll relatively about the stent assembly 33.

As shown in FIGS. 12 and 14, crimper body 36 provides a bore portion 37 formed and dimensioned for rotating receipt of the roller housing 80 and the crimp roller 28 therein as a unit. Bore portion 37 preferably includes a widened chamber portion 82 generally cylindrical shaped in the transverse cross-sectional dimension to accommodate the rotating crimp roller 28 rotatably mounted to the roller housing 80. Further, the roller housing and the crimp roller, as the combination thereof, rotates about the chamber portion of the crimper body as a unit.

In this embodiment, an access opening 83 into bore portion 37 is positioned at the distal end of crimper body 36 which is formed for rotatable receipt of a crimper knob 45 of the roller housing (FIG. 12). Preferably, a bearing portion 42 of crimper knob 45 includes an annular shoulder portion 85 rotatably retained in an annular pocket 86 at the access opening 83. The proximal end of the roller housing 80 includes a post portion 71 rotatably received in a cylindrical cavity 87 at the end of bore portion 37. Collectively, the roller housing and the crimp roller 28 rotate about the roller housing longitudinal axis 88 as the crimper knob 45 is manually or mechanically rotated relative the crimper body 36.

The roller housing 80 defines a recess portion 90 formed for rotatable receipt of the crimp roller 28 therein at an orientation positioning the first compression wall 27 opposite the second compression wall 30 of the crimp roller 28. A mounting shaft 91 extends through the longitudinal axis of the crimp roller 28 to rotatably position the same substantially parallel to the first compression wall 27. Thus, when the roller housing 80 is rotatably mounted in the bore portion 37 of the crimper body 36, the crimp roller 28 can further be rotated together with the roller housing as a unit about the chamber portion 82 thereof.

To driveably couple the crimp roller 28 to the roller housing 80, the drive mechanism 81 includes an internal ring gear 72 coupled to the crimper body in the bore portion 37 (FIGS. 12, 13A and 13B). In the preferred embodiment, ring gear 72 is fixedly positioned in an annular slot 92 of bore portion 37 in a manner communicating the inwardly facing teeth with the bore portion 37. A drive gear 70, rotatably mounted to the roller housing 80 through mounting shaft 91, driveably engages the teeth of the ring gear 72 as the roller housing 80 and the crimp roller rotate about the bore portion as a unit. Preferably, the drive gear 70 drives the crimp roller 28 (via mounting shaft 91) on a 1:1 rotating ratio. It will be understood, of course, that this figure may vary.

Referring now to FIGS. 13A and 13B, by rotating roller housing 80 (via crimper knob 45) relative crimper body 36 in the direction of arrow 47, for example, the drive gear 70 engaging the teeth of the ring gear 72 is caused to rotate in the opposite direction of arrow 93. The drive gear 70 rotatably drives the mounting shaft 91 which in turn rotatably drives the crimp roller 28 about the shaft axis (FIGS. 14A and 14B), also in the direction of arrow 47. Consequently, the first compression wall 27 of the roller housing 80 and the second compression wall 30 of the crimp roller 28 cooperate to compressively roll the elastic tube 23 and/or the uncrimped stent assembly 33 between the first position (FIG. 14A) and the second position (FIG. 14B).

Similar to the previous embodiments, the crimp roller 28 may include a recessed wall portion 57 to increase the gap distance between the first and second compression walls to form insertion cavity 48 at the first position (FIG. 14A).

Moreover, the first compression wall 27 preferably defines a longitudinally extending groove portion 50 formed and dimensioned for receipt of the elastic tube and/or the uncrimped stent assembly 33 therein. Thus, when the recessed wall portion 57 of the crimp roller 28 is aligned opposite the groove portion 50 of the roller housing, the uncrimped stent assembly may be slideably positioned therebetween.

Groove portion 50 is preferably semi-circular in shape and is diametrically sized to receive the elastic tube 23 therein. During the crimping procedure, the groove portion facilitates maintaining the longitudinal alignment of the elastic tube and the stent assembly in between the first and second compression walls. Moreover, as shown in FIG. 12, an alignment cavity 95 is provided at the distal end of the groove portion 50 for sliding receipt of the distal tip 60 of the elastic tube 23 and stent assembly 33 therein during crimping. As the crimp roller 28 and groove portion 50 of the first compression wall 27 cooperate to crimp the stent assembly in the second position, the alignment cavity 95 rotatably receive the same to maintain longitudinal alignment.

In accordance with this embodiment of the present invention, the roller housing 80 and the rotating crimp roller 28 rotate about the stent assembly 33 as a unit during the crimping procedure. This is preferably performed by positioning the longitudinal axis of the stent assembly substantially co-axial with the longitudinal axis 88 of the roller housing 80 (FIGS. 13A and 13B) about which the roller housing rotates during crimping. The stent assembly 33 can therefore be maintained relatively stationary as the crimp roller 28 rotates between the first and second positions.

As the crimp roller 28 rotates relative the first compression wall 27, the elastic tube is caused to be compressively rolled therebetween to crimp the stent assembly. However, since the crimp roller 28 is actually rolling about the elastic tube 23, the elastic tube 23 rotates in the groove portion 50 so that the stent assembly is maintained relatively stationary during rotative crimping.

To facilitate positioning of the stent assembly 33 in substantial co-axial relation s with the longitudinal axis 88 of the roller housing 80, an access port 96 is provided at the proximal end of the crimper body 36 which extends into bore portion 37. FIG. 12 illustrates that the crimper body access port 96 is further substantially axially aligned with a receiving port 97 extending through the post portion 71 of roller housing 80 which is further axially aligned with the groove portion 50 formed in the first compression wall.

Accordingly, a proboscis 67 of a radiation shield 55 may be slideably inserted into the access port 96 of the crimper body to deliver the uncrimped stent assembly therethrough. As the stent assembly 33 is further urged through the access port 96, the stent assembly is slideably received in the receiving port 97 of the roller housing post portion 71. Finally, the stent assembly, when the loading apparatus is in the first position, is positioned into the groove portion 50 of the first compression wall 27 until the distal tip 60 thereof is slideably received in the alignment cavity 95. Rotatable compressive crimping may then commence.

In an alternative configuration of the above-mentioned fifth embodiment, a dual crimp roller arrangement 20 is provided having a pair of opposed crimp rollers 28, 28' (FIGS. 16A and 16B) which cooperate to crimp the stent 21 onto the deployment device 22. In this embodiment, the first compression wall 27 is provided by the opposed crimp roller 28' rotatably coupled to the roller housing 80. The first compression wall 27 of the opposed crimp roller 28' further is substantially cylindrical-shaped and positioned adjacent and substantially parallel to the substantially cylindrical second compression wall 30 of the first crimp roller 28. The drive mechanism 81 is coupled between the opposed crimp rollers 28, 28' and the roller housing 80 for relative rotation of the second compression wall 30 and the first compression wall 27 between a first position (FIGS. 15A and 16A) and a second position (FIGS. 15B and 16B). In the first position, the first compression wall 27 and the second compression wall 30 are sufficiently spaced to enable receipt of the deformable stent 21 therebetween. In the second position, the opposed first and second compression walls are sufficiently spaced to roll and radially compress the stent 21 onto the deployment device 22.

The uncrimped stent assembly 33 is preferably positioned in an elastic tube 23 which facilitates rolling between the opposed compression walls and provides a protective barrier against damage thereof. Thus, the elastic tube 23 is positioned for compressive rolling contact between the first compression wall 27 and the second compression wall 30.

The drive mechanism 81 rotatably couples the crimper body 36 to the roller housing 80 such that upon relative simultaneous rotation between the crimper body 36 and the roller housing, the opposed crimp rollers 28, 28' are caused to compressively roll relatively about the stent assembly 33. Further, it will be appreciated that the diameters of the opposed crimp rollers 28, 28' are substantially the same, and that they rotate at substantially the same rotational speed, as dictated by drive mechanism and as will be described in greater detail below.

FIG. 16 illustrates that the generally cylindrical, widened chamber portion 82 of the bore portion 37 is dimensioned to accommodate both rotating crimp rollers 28, 28' in the crimper body 36, and which are rotatably mounted to the roller housing 80. Similar to the fifth embodiment of FIG. 12, the roller housing and the opposed crimp rollers, as the combination thereof, rotate about the chamber portion of the crimper body as a unit. Further, the roller housing and the opposed crimp rollers simultaneously rotate about the roller housing longitudinal axis 88 as the crimper knob 45 (as shown in FIG. 12) is manually or mechanically rotated relative the crimper body 36.

The roller housing 80 defines a recess portion 90 formed for rotatable receipt of opposed crimp rollers 28, 28' therein at an orientation positioning the first compression wall 27 of the opposed crimp roller 28' opposite the second compression wall 30 of the crimp roller 28. Respective mounting shafts 91, 91' extend through respective longitudinal axes of the opposed crimp rollers 28, 28' to rotatably position the same substantially parallel to the first compression wall 27 and the second compression wall 30. Thus, when the roller housing 80 is rotatably mounted in the bore portion 37 of the crimper body 36, the opposed crimp rollers 28, 28' can further be simultaneously rotated together with the roller housing as a unit about the chamber portion 82 thereof.

Figure 15A:
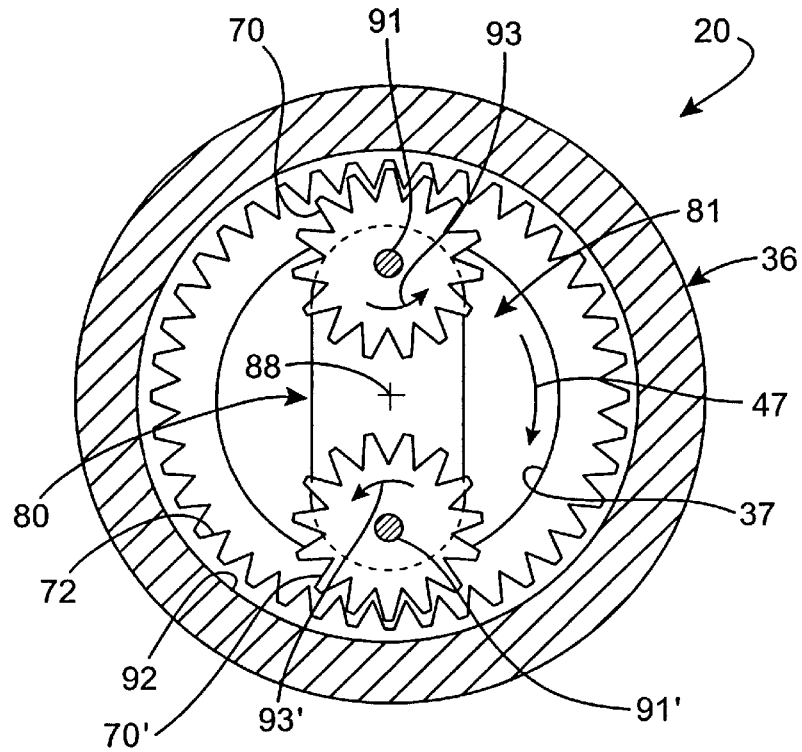
FIGS. 15A and 15B are a sequence of enlarged front elevation views, in cross-section., of a dual, opposed crimp roller embodiment of the stent loading apparatus of FIG. 12, taken substantially along the plane of the line 13—13 in FIG. 12, and illustrating a dual gear assembly during crimping movement between the first position and the second positions.
Figure 15B:
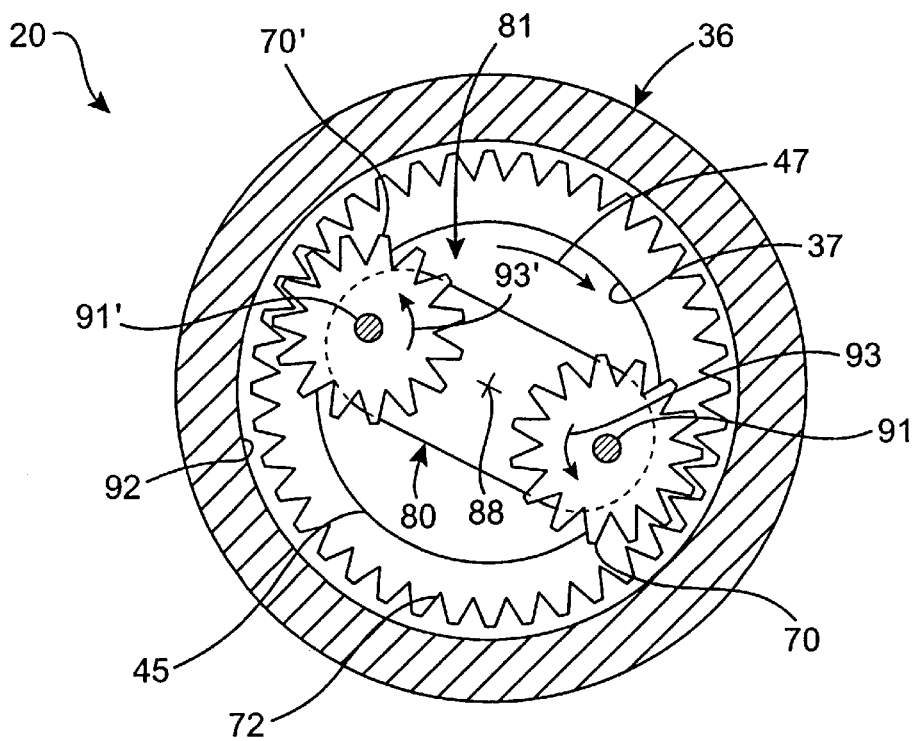

Referring now to FIGS. 15A and 15B, to driveably couple the opposed crimp rollers 28, 28' to the roller housing 80, the drive mechanism 81 includes a pair of internal drive gears 70, 70' rotatably mounted to the roller housing 80 through mounting shafts 91, 91'. These internal drive gears simultaneously driveably engage the teeth of the ring gear 72 as the roller housing 80 and the crimp roller rotate about the bore portion as a unit. Preferably, the opposed drive gears 70, 70' are similarly sized to simultaneously drive the opposed crimp rollers 28, 28' (via mounting shafts 91, 91') at substantially the same rotational speed.

For example, by rotating roller housing 80 (via crimper knob 45) relative crimper body 36 in the direction of arrow 47, the opposed drive gears 70, 70' engaging the teeth of the ring gear 72 are caused to rotate in the opposite direction of arrows 93, 93'. The drive gears 70, 70' rotatably drive the respective mounting shafts 91, 91' which in turn rotatably drive the respective crimp roller 28, 28' (FIGS. 16A and 16B), also in the direction of arrow 47. Consequently, the first compression wall 27 of crimp roller 28' and the second compression wall 30 of crimp roller 28 cooperate to compressively roll the elastic tube 23 and/or the uncrimped stent assembly 33 between the first position (FIG. 16A) and the second position (FIG. 16B).

Figure 16A:
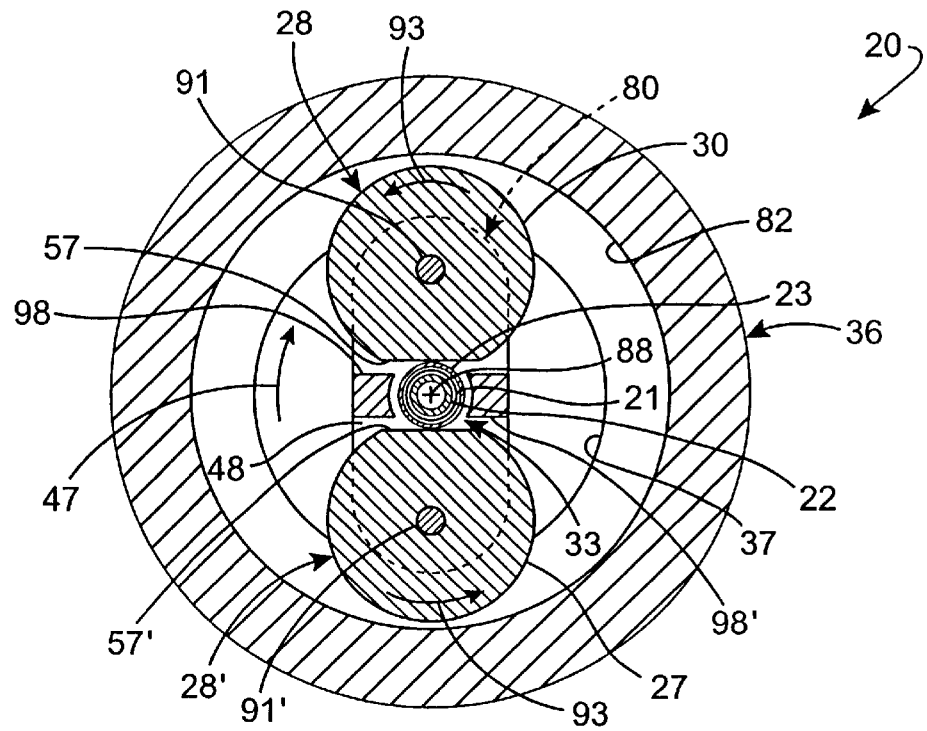
FIGS. 16A and 16B are a sequence of enlarged front elevation views, in cross-section, of the dual, opposed crimp roller embodiment of stent loading apparatus of FIG. 12, taken substantially along the plane of the line 14—14 in FIG. 12, and illustrating the dual crimp rollers engaging the stent during crimping movement between the first position and the second positions.
Figure 16B:
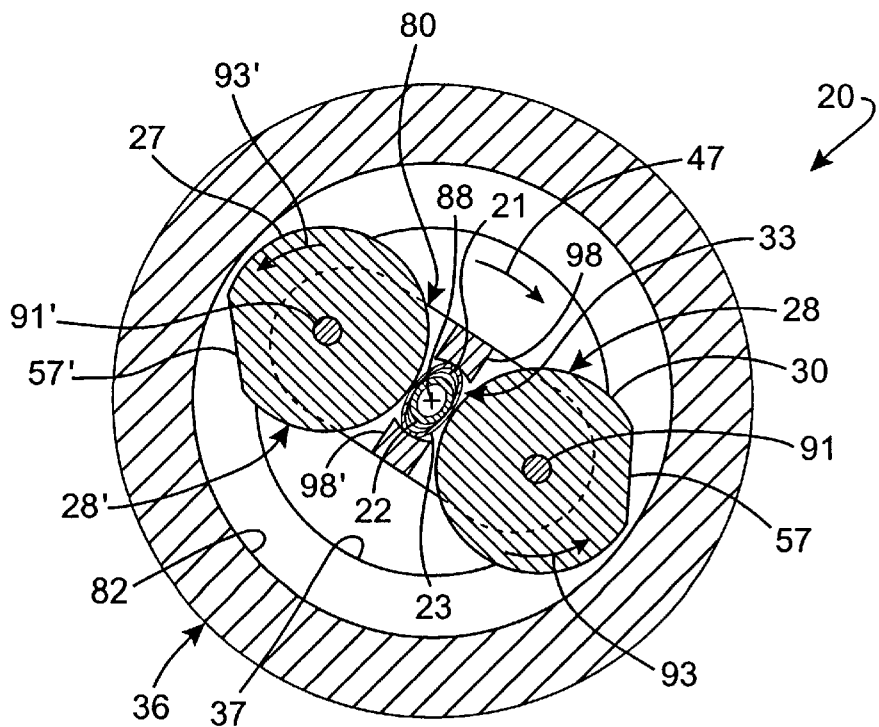

Similar to the previous embodiments, each crimp roller 28, 28' may include recessed wall portions 57, 57' to increase the gap distance between the first and second compression walls to form insertion cavity 48 at the first position (FIG. 16A). Thus, when the recessed opposed wall portions 57, 57' of respective crimp rollers 28, 28' are aligned, the uncrimped stent assembly may be slideably positioned therebetween.

To facilitate positioning of the elastic tube 23 and the stent assembly 33 in substantial coaxial alignment with the rotational axis 88 of the roller housing 80, an opposed pair of longitudinally extending alignment posts 98, 98' are provided substantially parallel to the rotational axis. During the crimping procedure, these alignment posts 98, 98' facilitate maintaining the longitudinal alignment of the elastic tube and the stent assembly in between the first and second compression walls during crimping. Moreover, as provided in the previous embodiment of FIG. 12, an alignment cavity 50 is provided at the distal ends of the alignment posts for sliding receipt of the distal tip 60 of the elastic tube 23 and stent assembly 33 therein during crimping. As the opposed crimp rollers 28, 28' and the opposed alignment posts 98, 98' cooperate to crimp the stent assembly in the second position (FIG. 16B), the alignment cavity rotatably receive the same to maintain longitudinal alignment.

What is claimed is:

1. A stent loading apparatus for loading a deformable stent onto a deployment device comprising:

an elastic member defining a passage therein formed for longitudinal receipt of the deformable stent in an uncrimped condition;

a first member having a first compression region; and a second member having a second compression region positioned substantially adjacent said first compression region at a first position enabling receipt of the elastic member and the deformable stent in the uncrimped condition therebetween, said first compression region and said second compression region configured for rolling support and compression of said elastic member during relative movement between the first position and a second position to radially compress said deformable stent onto the deployment device.

2. The stent loading apparatus according to claim 1 wherein, said second member includes a crimp roller providing said second compression region substantially cylindrical in shape, and adapted rotate about the elastic member between the first position and the second position.

3. The stent loading apparatus according to claim 2 wherein, said crimp roller is rotatably coupled to said first member such that said second compression region rotates relative said first compression region.

4. The stent loading apparatus according to claim 3 wherein, said first member defines a bore formed for rotational receipt of said crimp roller between the first position and the second position.

5. The stent loading apparatus according to claim 4 wherein, said first compression region includes interior walls positioned opposite the second compression region of said crimp roller to form a substantially cylindrical-shaped bore.

6. The stent loading apparatus according to claim 5 wherein, the longitudinal axis of said crimp roller is substantially co-axial with the longitudinal axis of said bore such that said second compression region of said crimp roller and said first compression region defining the cylindrical bore are substantially concentric.

7. The stent loading apparatus according to claim 6 further including:

a gear assembly cooperating with said first member, said second member and said deployment device for rolling support of said elastic member between the first position and the second position.

8. The stent loading apparatus according to claim 7 wherein, said gear assembly includes a drive gear coupled to said second member, and a spur gear coupled to said deployment device and driveably meshed with said drive gear to facilitate movement of said elastic member between the first position and the second position.

9. The stent loading apparatus according to claim 8 wherein, said gear assembly further includes an internal gear coupled to said first member and positioned such that said spur gear is driveably meshed between said drive gear and said internal gear.

10. The stent loading apparatus according to claim 9 wherein, said drive gear is co-axial with the crimp roller longitudinal axis and with the longitudinal axis of said internal gear.

11. The stent loading apparatus according to claim 9 wherein, said gear assembly further includes a second spur gear positioned between the drive gear and said internal gear, spaced-apart from the first named spur gear.

12. The stent loading apparatus according to claim 9 wherein, said spur gear defines an aperture extending therethrough for sliding receipt of said deployment device therein.

13. The stent loading apparatus according to claim 12 further including:

a luer lock device configured to mate with said spur gear during movement between the first position and the second position.

14. The stent loading apparatus according to claim 5 wherein, said bore extends longitudinally into said first member from one end thereof, and first member further defining a port extending into said bore from an opposite end of said first member, and said second member includes a bearing portion extending through said port terminating at said crimp roller in said bore such that rotation of said bearing portion relative said first member rotates said second compression region relative said first compression region.

15. The stent loading apparatus according to claim 5 wherein, said second compression region of said crimp roller includes a longitudinally extending groove formed and dimension for receipt of said elastic member therein for rolling support thereof between the first position and the second position.

16. The stent loading apparatus according to claim 5 wherein, said second compression region includes a recess portion cooperating with said first compression region to form a cavity at the first position sufficiently sized to enable longitudinal insertion of the stent in the uncrimped condition in the elastic member.

17. The stent loading apparatus according to claim 16 wherein, the longitudinal axis of said crimp roller is substantially co-axial with the longitudinal axis of said bore such that said second compression region of said crimp roller and said first compression region defining the cylindrical bore are substantially concentric.

18. The stent loading apparatus according to claim 17 wherein, said second compression region of said crimp roller includes a longitudinally extending groove formed and dimension for receipt of said elastic member therein for rolling support thereof between the first position and the second position.

19. The stent loading apparatus according to claim 16 wherein, the longitudinal axis of said crimp roller is substantially parallel to and offset from the longitudinal axis of said bore such that said second compression region of said crimp roller and said first compression region defining the cylindrical bore are rotatably off-set from one another.

20. The stent loading apparatus according to claim 5 further including:

a radiation shield coupled to said deployment device and formed for positioning proximate an opening into said bore during movement of said second member between the first and second positions.

21. The stent loading apparatus according to claim 3 wherein, said first compression region includes a longitudinally extending groove formed and dimension for receipt of said elastic member therein for rolling support thereof between the first position and the second position.

22. The stent loading apparatus according to claim 22 further including:

a drive mechanism coupled to said crimp roller for rotation thereof relative said first compression region.

23. The stent loading apparatus according to claim 23 wherein:
said drive mechanism includes a drive gear driveably coupled to said crimp roller for rotation thereof relative said first compression region.

24. The stent loading apparatus according to claim 25 further including:
a crimper body rotatably coupled to said first member through said drive gear.

25. The stent loading apparatus according to claim 24 wherein:
said crimper body defines a bore portion formed and dimensioned for rotating receipt of said first member and said crimp roller therein, and
said drive mechanism includes an internal ring gear coupled to said crimper body in said bore portion, and driveably engaged with said drive gear such that rotation of said crimper body relative said first member drives said crimp roller between the first position and the second position.

26. The stent loading apparatus according to claim 25 wherein:
said first member includes
a roller housing positioned in said bore, and defining a recess formed for rotatable receipt of said crimp roller therein at an orientation positioning said first compression region opposite said second compression region, and
a crimper knob extending from said bore, and rotatably coupled to said crimper body for relative rotation between said first member, said second member and said crimper body.

27. The stent loading apparatus according to claim 1 further including:
a shrink tube shrunk fit and secured longitudinally around the stent in the uncrimped condition, and formed for sliding receipt of the deployment device therethrough.

28. The stent loading apparatus according to claim 1 further including:
a shrink tube shrunk fit and secured longitudinally around the stent in the uncrimped condition, and formed for sliding receipt of the deployment device therethrough.

29. A stent crimping apparatus for loading a deformable stent onto a deployment device comprising:
a crimper body including a curvilinear first compression wall defining a bore portion; and
a spindle member having an independent, curvilinear second compression wall extending into said bore portion adjacent said first compression wall, said spindle member is rotatably coupled to said crimper body for relative rotation of the first compression wall and the second compression wall between a first position, enabling receipt of the deformable stent therebetween in an uncrimped condition, and a second position, to roll and radially compress therebetween said stent onto the deployment device.

30. The stent crimping apparatus according to claim 29 wherein,
said first compression wall is substantially cylindrical, and
said spindle member includes a substantially cylindrical crimp roller portion, providing said second compression wall, and adapted rollingly contact and compress said stent the first position and the second position.

31. The stent crimping apparatus according to claim 30 wherein,
the longitudinal axis of said crimp roller is substantially co-axial with the longitudinal axis of said bore such that said second compression wall of said crimp roller and said first compression wall defining the cylindrical bore are substantially concentric.

32. The stent crimping apparatus according to claim 31 wherein,
one of said second compression wall and said first compression wall includes a longitudinally extending groove at the first position formed and dimension for longitudinal receipt of said stent therebetween, in an uncrimped condition.

33. The stent crimping apparatus according to claim 31 wherein,
said crimp roller includes a recess portion cooperating with said first compression wall to form a cavity at the first position sufficiently sized to enable longitudinal insertion of the stent therein in an uncrimped condition.

34. The stent crimping apparatus according to claim 31 further including:
a gear assembly cooperating with said crimper body, said spindle member and said deployment device for rolling support of said stent between the first position and the second position.

35. The stent crimping apparatus according to claim 34 wherein,
said gear assembly includes a drive gear coupled to said crimp roller, an internal gear coupled to said crimper body, and a spur gear driveably meshed between said drive gear and said internal gear and coupled to said deployment device to facilitate movement of said stent between the first position and the second position.

36. The stent crimping apparatus according to claim 35 wherein,
said drive gear is co-axial with the crimp roller longitudinal axis and with the longitudinal axis of said internal gear.

37. The stent crimping apparatus according to claim 36 wherein,
said gear assembly further includes a second spur gear meshed with and positioned between the drive gear and said internal gear, spaced-apart from the first named spur gear.

38. The stent crimping apparatus according to claim 36 wherein,
said spur gear defines an aperture extending therethrough for sliding receipt of said deployment device therein.

39. The stent crimping apparatus according to claim 38 further including:
a luer lock device configured for receipt in said aperture of said spur gear during movement between the first position and the second position.

40. The stent crimping apparatus according to claim 30 wherein,
said crimper body includes a port longitudinally extending into said bore from one end thereof, and
said spindle member includes a bearing portion extending through said port terminating at said crimp roller in said bore such that rotation of said bearing portion relative said crimper body rotates said second compression wall relative said first compression wall.

41. The stent crimping apparatus according to claim 30 further including:

a radiation shield coupled to said deployment device and formed for positioning proximate an opening into the crimper body bore during movement between the first and second positions.

42. The stent crimping apparatus according to claim 30 wherein, the longitudinal axis of said crimp roller is substantially parallel to and offset from the longitudinal axis of said bore such that said second compression wall of said crimp roller and said first compression wall defining the cylindrical bore are rotatably off-set from one another.

43. A stent crimping apparatus for loading a deformable stent onto a deployment device comprising:

a roller housing having a first compression wall;

a crimp roller rotatably coupled to said roller housing, and having a substantially cylindrical, independent, second compression wall positioned adjacent and substantially parallel to said first compression wall; and a drive mechanism coupled between said crimp roller and said roller housing for relative rotation of said second compression wall and said first compression wall between a first position, enabling receipt of the deformable stent therebetween in an uncrimped condition, and a second position, to roll and radially compress therebetween said stent onto the deployment device.

44. The stent crimping apparatus according to claim 43 wherein:

said drive mechanism includes a drive gear driveably coupled to said crimp roller for rotation thereof relative said first compression wall.

45. The stent crimping apparatus according to claim 44 further including:

a crimper body rotatably coupled to said roller housing through said drive gear.

46. The stent crimping apparatus according to claim 45 wherein:

said crimper body defines a bore portion formed and dimensioned for rotating receipt of said roller housing and said crimp roller therein, and said drive mechanism includes an internal ring gear coupled to said crimper body in said bore portion, and driveably engaged with said drive gear such that rotation of said crimper body relative said roller housing drives said crimp roller between the first position and the second position.

47. The stent crimping apparatus according to claim 46 wherein:

said roller housing defines a recess formed for rotatable receipt of said crimp roller therein at an orientation positioning said first compression wall opposite said second compression wall, said roller housing further including a manually grippable crimper knob rotatably coupled to said crimper body for relative rotation of said roller housing, said crimp roller and said crimper body.

48. The stent crimping apparatus according to claim 43 wherein:

said first compression wall defines a longitudinally extending groove portion formed and dimensioned for longitudinal receipt of the deformable stent during crimping.

49. The stent crimping apparatus according to claim 48 wherein:

said roller housing farther includes an alignment cavity positioned in distal alignment with the groove portion for longitudinal receipt of a tip portion of the deployment device therein when the deformable stent is received in the groove portion.

50. A stent apparatus for use with loading a stent onto a deployment device comprising:

an uncrimped elongated stent having an uncrimped diameter; and a shrink tube having a longitudinal length longer than said stent, and having an unshrunk diameter, in an unshrunk condition, larger than the uncrimped diameter of the stent for sliding receipt of the stent therein, and a shrunk diameter, in a shrink condition, smaller than said uncrimped diameter to secure said shrink tube longitudinally around the stent for support thereof to facilitate positioning and alignment of the deployment device in the uncrimped stent.

51. The stent apparatus as defined in claim 50 wherein, shrink tube is configured to have shrunk diameter larger a diameter of said stent in a crimped condition.

52. A method of crimping a stent in an uncrimped condition onto a deployment device comprising the steps of:

inserting the uncrimped stent into an elastic tube having a diameter larger than the diameter of the uncrimped stent;

compressing said elastic tube until the opposed interior walls of said elastic tube contact the exterior walls of the uncrimped stent;

compressibly rolling said elastic tube and said uncrimped stent from an uncrimped condition to a crimped condition until the compressed stent is mounted to the deployment device.

53. The method according to claim 52 wherein, said rolling step by rolling said elastic tube and said stent back and forth.

54. The method according to claim 52 wherein, said rolling step by rolling said elastic tube and said stent in one direction.

55. A shielded stent crimping assembly for loading a radioactive stent onto a deployment device comprising:

a crimping mechanism adapted to crimp the radioactive stent onto the deployment device; and a shielded crimper body defining a bore portion formed for receipt of said radioactive stent and said crimping mechanism therein, said crimper body and said crimping mechanism cooperating to substantially prevent the passage of radiation from said bore portion during crimping of the stent by the crimping mechanism.

* * * * *